US007087740B2

(12) United States Patent
El Solh et al.

(10) Patent No.: US 7,087,740 B2
(45) Date of Patent: *Aug. 8, 2006

(54) KITS FOR USE IN DETECTING RESISTANCE TO STREPTOGRAMIN A AND RELATED COMPOUNDS

(75) Inventors: Névine El Solh, Vincennes (FR); Jeanine Allignet, Nanterre (FR)

(73) Assignee: Institut Pasteur, Paris (FR)

( * ) Notice: Subject to any disclaimer, the term of this patent is extended or adjusted under 35 U.S.C. 154(b) by 240 days.

This patent is subject to a terminal disclaimer.

(21) Appl. No.: 10/253,904

(22) Filed: Sep. 25, 2002

(65) Prior Publication Data

US 2003/0158135 A1 Aug. 21, 2003

Related U.S. Application Data

(63) Continuation of application No. 09/446,301, filed as application No. PCT/IB98/00962 on Jun. 22, 1998, now Pat. No. 6,506,893.

(60) Provisional application No. 60/050,380, filed on Jun. 20, 1997.

(51) Int. Cl.
*C07H 21/04* (2006.01)
(52) U.S. Cl. ............... 536/23.7; 424/234.1; 424/244.1; 435/6; 435/7.2; 435/69.1; 435/91.2; 536/23.1
(58) Field of Classification Search .................... 435/6, 435/7.2, 69.1, 91.2; 536/23.3, 231; 424/234.1, 424/244.1
See application file for complete search history.

(56) References Cited

U.S. PATENT DOCUMENTS

| 5,468,852 | A | * | 11/1995 | Ohashi et al. | ........... 536/24.33 |
| 5,635,348 | A | * | 6/1997 | Leong | ............................. 435/6 |
| 5,994,066 | A | | 11/1999 | Bergeron et al. | ............... 435/6 |
| 6,001,564 | A | | 12/1999 | Bergeron et al. | ............... 435/6 |

FOREIGN PATENT DOCUMENTS

WO WO 96/08582 3/1996

OTHER PUBLICATIONS

Riffkin et al. A single amino-acid change between the antigenically different extracellular serine protease V2 and B2 from Dichelobacter nodous. Gene (1955) vol. 167, pp. 279-283.*
Zhang et al. Detection of *Streptococcus pneumoniae* in whole blood PCR. Journal of Clinical Microbiology (1995) vol. 33, N 3, pp. 596-601.*
Allignet, et al. "Sequence of a staphylococcal plasmid gene, vga, encoding a putative ATP-binding protein involved in resistance to virginiamycin A-like antibiotics" *Gene* vol. 117 (1992) pp. 45-51.

Allignet, et al. "Sequence of a staphylococcal gene, vat, encoding an acetyltransferase inactivating the A-type compounds of virginiamycin-like antibiotics" *Gene* vol. 130 (1993) pp. 91-98.
Jeanine Allignet and Névine El Solh "Diversity among the Gram-Positive Acetyltransferases Inactivating Streptogramin A and Structurally Related Compounds and Characterization of a New Staphylococcal Determinant, vatβ" *Antimicrobial Agents and Chemotherapy* vol. 39. No. 9 (Sep. 1995) pp. 2027-2036.
Jeanine Allignet and Névine El Solh "Characterization of a new staphylococcal gene, vga β. encoding a putative ABC transporter conferring resistance to streptogramin A and related compounds" *Gene* vol. 202 (1997) pp. 133-138.
Jeanine Allignet, et al. "Distribution of Genes Encoding Resistance to Treptogramin A and Related Compounds among Staphylococci Resistant to These Antibiotics" *Antimicrobial Agents and Chemotherapy* vol. 40. No. 11 (Nov. 1996) pp. 2523-2528.
Jeanine Allignet, Névine El Solh, et al. "Nucleotide Sequence of a Staphylococcal Plasmid Gene. vgb, Encoding a Hydrolase Inactivating the B Components of Virginiamycin-like Antibiotics" *Plasmid* vol. 20 (1988) pp. 271-275.
Marc Aumercier, et al. "RP 59500: a proposed mechanism for its bactericidal activity" *Jountal of Antimicrobial Chemotherapy* vol. 30, Supp. A (1992) pp. 9-14.
N. El Solh, et al. "Epidemiological and Structural Studies of *Staphylococcus aureus* R Plasmids Mediating Resistance to Tobramycin and Streptogramin" *Plasmid* vol. 4 (1980) pp. 117-120.
Maria Inmaculada Barrasa, et al. "The ard1 gene from *Stretomyces capreolus* encodes a polypeptide of the ABC-transporters superfamily which confers resistance to the aminonucleoside antibiotic A201A" *European Journal of Biochemistry* vol. 228 (1995) pp. 562-569.
Veronique Blanc, et al. "Molecular characterization and transcriptional analysis of a multidrug resistance gene cloned from the pristinamycin-producing organism, *Streptomyces pristinaespirals*" *Molecular Microbiology* vol. 17, No. 5 (1995) pp. 989-999.

(Continued)

*Primary Examiner*—Ulrike Winkler
(74) *Attorney, Agent, or Firm*—Finnegan, Henderson, Farabow, Garrett & Dunner, L.L.P.

(57) ABSTRACT

A kit for use in detecting a bacterium having resistance to streptogramin A and related compounds is provided. A kit for use in detecting a bacterium harboring at least one polynucleotide encoding VgaB in a biological sample is also provided. The kits comprise at least one oligonucleotide probe and at least one reagent for performing a nucleic acid hybridization reaction.

12 Claims, 11 Drawing Sheets

OTHER PUBLICATIONS

C. Cocito "Antibiotics of the Virginiamycin Family, Inhibitors Which Contain Synergistic Components" *Microbiological Reviews* vol. 43, No. 2 (Jun. 1979) pp. 145-198.

M. Di Giambattista, et al. "The molecular basis of the inhibitory activities of type A and type B synergimycins and related antibiotics on ribosomes" Journal of Antimicrobial Chemotherapy vol. 24 (1989) pp. 485-507.

K.G.H. Dyke and S.P. Curnock "The nucleotide sequence of a small cryptic plasmid found in *Staphylococcus aureus* and its relationship to other plasmids" *FEMS Microbiology Letters* vol. 58 (1989( pp. 209-216.

J.M. Entenza, et al. "Treatment of Experimental Endocarditis Due to Erythromycin-Susceptible or Resistant Methicillin-Resistant *Staphylococcus aureus* with RP 59500" *Antimicrobial Agents and Chemotherapy* vol. 39, No. 7 (Jul. 1995) pp. 1419-1424.

Bruno Fantin, et al. "Critical influence of Resistance to Streptogramin B-Type Antibiotics on Activity of RP 59500 (Quinupristin-Dalfopristin) in Experimental Endocarditis Due to *Staphylococcus aureus*" *Antimicrobial Agents and Chemotherapy* vol. 39, No. 2 (Feb. 1995) pp. 400-405.

J. Fernando Fierro, et al. "Streptogramins-inactivating activity in three producer streptomycetes" *FEMS Microbiology Letters* vol. 58 (1989) pp. 243-246.

Martin Geistlich, et al. "Characterization of a novel regulatory gene governing the expression of a polyketide synthase gene in *Streptomyces ambofaciens*" *Molecular Microbiology* vol. 6, No. 14 (1992) pp. 2019-2029.

Maria Griswold, et al. "Quinupristin-dalfopristin (RP 59500): An injectable streptogramin combination" *Am J Health-Syst Pharm* vol. 53 (Sep. 1996) pp. 2045-2053.

Stephen Hyde, et al. "Structural model of ATP-binding proteins associated with cystic fibrosis, multidrug resistance and bacterial transport" *Nature* vol. 346 (Jul. 1990) pp. 362-365.

Jack Kyte and Russell Doolittle "A Simple Method for Displaying the Hydropathic Character of a Protein" *Journal of Molecular Biology* vol. 157 (1982) pp. 105-132.

Chang Han Kim, et al. "Studies on Mikamycin B. lactonase: I. Degradation of Mikamycin B by *Streptomyces Mitakaensis*" *The Journal of Antibiotics* vol. XXVII No. 12 (Dec. 1974) pp. 903-908.

Takeshi Kimura, et al. "Selective unfolding of erythroid chromatin in the region of the active β-globin gene" *Nature* vol. 306 (Dec. 1983) pp. 709-712.

Nadia Liassine, Jeanine Allignet, Névine El Solh, et al. "Multiplicity of the Genes and Plasmids Conferring Resistance to Pristina- mycin in Staphylococci Selected in an Algerian Hospital" *Zentralblatt für Bakteriologie* vol. 286 (1997) pp. 389-399.

Jane McLaughlin, et al. "Unique Features in the Ribosome Binding Site Sequence of the Grampositive *Staphylococcus aureus* β-Lactamase Gene" *The Journal of Biological Chemistry* vol. 256 No. 21 (Nov. 1981) pp. 11283-11291..

V. Loncle, N. El Solh, et al. "Analysis of Pristinamycin-Resistant *Staphylococcus epidermidis* Isolates Responsible for an Outbreak in a Parisian Hospital" *Antimicrobial Agents and Chemotherapy* vol. 37, No. 10 (Oct. 1993) pp. 2159-2165.

Claudia Meyer, et al. "Nucleotide sequence of the lantibiotic Pep5 biosynthetic gene cluster and functional analysis of PepP and PepC—Evidence for a role of PepC in thioether formation" *European Journal of Biochemistry* vol. 232 (1995) pp. 478-489.

Charles Moran, Jr., et al. "Nucleotide Sequences that Signal the Initiation of Transcription and Translation in *Bacillus subtilis*" *Mol. Gen. Genet.* vol. 186 (1982) pp. 339-346.

Carlos Orlando, et al. "A second ABC transporter is involved in oleandomycin resistance and its secretion by *Streptomyces antibioticus*" *Molecular Microbiology* vol. 16, No. 2 (1995) pp. 333-343

Ursula Peschke, et al. "Molecular characterization of the lincomycin-production gene cluster of *Streptomyces lincolnensis* 78-11" *Molecular Microbiology* vol. 16, No. 6 (1995) pp. 1137-1156.

Rosanna Rende-Fournier, et al. Identification of the satA Gene Encoding a Streptogramin A Acetyltransferase in *Enterococcus faecium* BM4145 *Antrimicrobial Agents and Chemotherapy* vol. 37, No. 10 (Oct. 1993) pp. 2119-2125.

J.I. Ross, et al. "Inducible erythromycin resistance in staphylococci is enclosed by a member of the ATP-binding transport super-gene family" *Molecular Microbiology* vol. 4, No. 7 (1990) pp. 1207-1214.

Jeremy Ross, et al. "Identification of a chromosomally encoded ABC-transport system with which the staphylococcal erythromycin exporter MsrA may interact" *Gene* vol. 153 (1995) pp. 93-98.

Jeremy Ross, et al. "Minimal functional systems required for expression of erythromycin resistance by *msrA* in *Staju;pcpccis aireis* RN4220" *Gene* vol. 183 (1996) pp. 143-148.

Paul Rosteck, Jr., et al. "Homology between proteins controlling *Streptomyces fradiae* tylosin resisstance and ATP-binding transport" *Gene* vol. 102 (1991) pp. 27-32.

Brigitte Schoner, et al. "Sequence similarity between macrolide-resistance determinants and ATP-binding transport proteins" *Gene* vol. 115 (1992) pp. 93-96.

F. Sanger, et al. "DNA sequencing with chain-terminating inhibitors" *Proc. Natl. Academy Sci. USA Biochemistry* vol. 74, No. 12 (Dec. 1977) pp. 5463-5467.

E.M. Southern "Detection of Specific Sequences Among DNA Fragments Separated by Gel Electrophoresis" *Journal of Molecular Biology* vol. 98 (1975) pp. 503-517.

Ignacio Tinoco, jun. et al. "Improved Estimation of Secondary Structure in Ribonucleic Acids" *Nature New Biology* vol. 246 (Nov. 1973) pp. 40-41.

Margarita Torralba, et al. "Treatment of Methicillin-Resistant *Staphylococcus aureus* Infection with Quinupristin/Dalfopristin" *Clinical Infectious Diseases* vol. 21 (1995) pp. 460-461.

Gunnar vol Heijne "A new method for predicting signal sequence cleavage sites" *Nucleic Acids Research*, vol. 14, No. 11 (1986) pp. 4683-4690.

John Walker, et al. "Distantly related sequences in the α- and β-subunits of ATP synthase, myosin, kinases and other ATP-requiring enzymes and a common nucleotide binding fold" *The EMBO Journal* vol. 1, No. 8 (1982) pp. 945-951.

Marion E.E. Watson "Compilation of published signal sequences" *Nucleic Acids Research* vol. 12, No. 13 (1984) pp. 5145-5164.

J. Allignet and N. El Solh "Sequence of a Staphylococcal Plasmid Gene *vgaB*, Encoding a Putative ATP-binding Protein Related to VGA Involved in Resistance to Streptogramin A" *National Reference Center for Staphlococci, Institut Pasteur* (P202) (1996).

Wesley Kloos and Karl Heinz Schleifer "Family I. Micrococcaceae, Section 12. Gram-Positive Cocci: *Genus IV. Staphylococcus Rosenbach 1884*, 18$^{AL}$" Nom. Cons. Opin. 17 Jud. Comm. (1958) 153, pp. 1013-1035.

* cited by examiner

SEQ. ID NO: 15

```
aagcttaattaagctagcagaagattatgggagttatgagtaatactagaagaacaagtgatagtgtactaagacaagcaaagatgataattgactattaaagagcaat      120
HindIII
tagaatatgaaaagatcgaaatgaaaactatcaaactttacgataatttattggaacagtgttagataattcaaagatatcagcaacaagattagtcttaatgatcaa         240
atagtatccaaaatgttagaatcagaattgtagaaggaatcagaataaaagagaaatcaaagaagaaactaagtgtatcatgtattccagagaaaaaatattatatattaaaatgagataaa    360
caaatgattagttgttttcaataggaatttgtaaaaccatgtacatataacttttaatttagtataaaatcaaagaaagggtgaaatattaataaaatgatcaaa         480
taatccgtcactaaaagaaaataaatatggaaagatttaacctaatatatttatgtctatttattgattggagtagtttgttatttgtatattccattataaactatcc       600
                                                                                                              SEQ ID NO: 50
                                                                                                              Start VgaB
                                                                                         RBS                   M L K I D M K
tctatttaaaaaggaggatttttttatgcttaaaatagacatgaag                                                                          720
                                                                                                                         Start VgaB
                M V K K Y Y A D K L I N I K E L K I Y S G D K I G I V  G K N G V G K T  L L K
aatgtaaaaaatattatgcagataaattaatcaataatagaactaaagattatgtggggataaaattaggtattgtaggtaagaataggagttggcaaaacaacactttaaaa     840
                I I K G L I E I D E G N I I S E K T T I K Y I S Q L E E P H S K I I D G K Y A
ataatgaaggactaatagagattgacgaaggaaatattatcagtgaaaaacaactattaaatatatctccaattagaagaaccacatagcaagataattgatggaaaatatgct   960
                S I F Q V E N K W N D N M S G G E K T R F K L A E G F Q D D Q C S  L M L V D  E P T
tcaatatttcaagttgaaaataagtggaatgacaatatgagtggtggtgaaaaaactagatttaagttggctgctatgtcttttatgctcgtagtgaacctaca          1080
                S N L D I E G I E L I T N T F K E Y R D T F L V V S H D R I F L D Q V C T K I F
agtaattagatcgaaggaatagagttgataacaatactttttaaagagtaccgtgatatctcatgatagaattttagataaagttgtacaaaattttt                   1200
                E I E N G Y I R E F I G N Y T N Y I E Q K E M L L R K Q E E Y E K Y N S K R K
gaaattgaaaatggatatattaggaattcatcgtaatttcatcaatctatagagcaacaagaaaatgcttcacgaagaaagaatacgaaaagtataattctaaaagaaag    1320
                        EcoRI
                Q L E Q A I K L K E N K A Q G M I K P P S K T M G T S E S R I W K M Q H A T K Q
caattggagcaagctataaagctaaaagagaataaggcgcaagaatgattaagcccccttcaaaaaacaatggaacatcgactctagaatatggaaaatatgcaacatgctactaaacaa   1440
                K K M H R N T K S L E T R I D K L N H V E K I K E L P S I K M D L P N R E Q F H
aaaagatgcatagatagacgaatacgaaatacgttggaaaacacgaatataatcatgtagaaaatcataaaagagcttcctttcttattaaatgattacctaatagagagcaatttcat    1560
                G R N V I S L K N L S I K F N N Q F L W R D A S F V I K G G E K V A I I  G N N G
ggtcgcaatgtaattagttatcaaaacttacttaaaaactttaaaatttaataatcttttggagagatgcttcattgtcattaaggtgcattaatggtaacaatggt         1680
                V G K T  L L K L I L E K V E S V I I S P S V K I G Y V S Q N L D V L Q S H K S
gtaggaaaaacaacattgttgaagctgttgatcttgagaaaagtagaatcagtaatatcaccatcagtaaattgatacgtcagtcagtcgtcgtacaatcctataaatct      1800
                                     XbaI
```

FIG. 2A

```
  I  L  E  N  V  M  S  T  S  I  Q  D  E  T  I  A  R  I  V  L  A  R  L  H  F  Y  R  N  D  V  H  K  E  I  N  V  L  S  G  G
  atcttagaaaatgtcatgtctacctccattccaagatgaacaatagcaagattgttctagcagattacattttatcgcaatgatgttcataagaaataatgtttgagtggtgga   1920

E  Q  I  K  V  A  F  A  K  L  F  V  S  D  C  N T L I L D  E  P  T  N  Y  L  D  I  D  A  V  E  A  L  E  E  L  L  I
  gaacaaataaaggttgctttgccaagctatttgttagcgattgtaatcattaattcttgatgaacaaactattggatcgttgaggcattagagaattgttaatt           2040

T  Y  E  G  V  V  L  F  A  S  H  D  K  K  F  I  Q  N  L  A  E  Q  L  L  I  E  N  N  K  V  K  K  F  E  G  T  Y  I  E
  acctatgaaggtgttgtgttatttgcttcccatgataaaaaattctataccaaaattgttaataatagaaaaaaatcgaaggaacatatagaa                       2160

Y  L  K  I  K  D  K  P  K  L  N  T  N  E  K  E  L  K  E  K  K  M  I  L  E  M  Q  I  S  L  L  S  K  I  S  M  E  E  N
  tatttaaaaataaaagataaaccaaaattaaatacaaatgaaaagaactcaaagaaaaagatgatactagaagtcaaattccatcattattaagtaaatcttcaatgaagaaaat  2280

E  E  K  N  K  E  L  D  E  K  Y  K  L  K  L  K  E  L  K  S  L  N  K  N  I  *                  M  K  Y  G
  gaagaaaaacaaaaagaattagatgaaaagtacaaagttaaaattgaaaattaaaataatattaaaataagcctaataaaaagcctaataagaattgaaaagcctaaaatgaaatatggcc P  D  P  N                                                          End VgaB                   Start VatB HaeIII
  ctgatccaat
       2411
```

FIG. 2B

```
         ┌─SEQ. ID NO: 4
         │                              WA
VgaB     └─-MLKIDMKNVKKYYADKLILNIKELKIYSGDKIGIVGKNGVGKTTLLKIIKGLIEIDEGN        59
Vga      ┌─MKIMLEGLNIKHYVQDRLLLNINRLKIYQNDRIGLIGKNGSGKTTLLHILYFKIVPEEG-         59
         │   *.*.*  *.*.***  **** .*.**..****.******.*.   *  .**
         └─SEQ. ID NO. 49
                                                        loop 3
VgaB     IIISEKTTIKYISQLEEPHSKIIDGKYASIFQVENKWNDNMSGGEKTRFKLAEGFQDQCS          119
Vga      -IVKQFSHCELIPQLKLIES------------------TKSGGEVTRNYIRQALDKNPE           99
         *. . .   * **   *                    .**** **  . .     .

WB
VgaB     LMLVDEPTSNLDIEGIELITNTFKEYRDTFLVVSHDRIFLDQVCTKIFEIENGYIREFIG         179
Vga      LLLADEPTTNLDNNYIEKLEQDLKNWHGAFIIVSHDRAFLDNLCTTIWEIDEGRITEYKG         159
         *.* ****.***    ** ..  *  .*..***** ***..** **.* **.*  *

VgaB     NYTNYIEQKEMLLRKQQEEYEKYNSKRKQLEQAIKLKENKAQGMIKPPSKTMGTSES--R         237
Vga      NYSNYVEQKELERHREELEYEKYEKEKKRLEKAINIKEQKAQRATKKP-KNLSLSEGKIK         218
         **.**.****.  .. .... *****  .*.**.** .**.*** * * *..   **   .

VgaB     IWKMQHATKQKKMHRNTKSLETRIDKLNHVEKIKELPSIKMDLPNREQFHGRNVISLKNL         297
Vga      GAKPYFAGKQKKLRKTVKSLETRLEKLESVEKRNELPPLKMDLVNLESVKNRTIIRGEDV         278
           *   * ****...  ******.**  *** ***.***** * *     ..*...*    .

WA
VgaB     SIKFNNQFLWRDASFVIKGGEKVAIIGNNGVGKTTLLKLILEKVESVIISPSVKIGYVSQ         357
Vga      SGTIEGRVLWKAKSFSIRGGDKMAIIGSNGTGKTTFIKKIVHGNPGISLSPSVKIGYFSQ         338
         *   .. ** ** *.**.****  ** **** .* *. ..  .****** **
                                                        loop 3'
VgaB     NLDVLQSHKSILENVMSTSIQDETIARIVLARLHFYRNDVHKEINVLSGGEQIKVAFAKL         417
Vga      KIDTLELDKSILENVQSSSQQNETLIRTILARMHFFRDDVYKPISVLSGGERVKVALTKV         398
          .* *.  ******* *.* **.**..* ****.**.* ***.** *.*.  ****..***.*.

WB
VgaB     FVSDCNTLILDEPTNYLDIDAVEALEELLITYEGVVLFASHDKKFIQNLAEQLLIIENNK         477
Vga      FLSEVNTLVLDEPTNFLDMEAIEAFESLLKEYNGSIIFVSHDRKFIEKVATRIMTIDNKE         458
         *.*. ***.******.**..**..**. ** *  ..* ***.***...*   ...  *.*

VgaB     VKKFEGTYIEYLKIKDKPKLNTNEKELKEKKMILEMQISSLLSKISMEENEEKNKELDEK         537
Vga      IKIFDGTY-EQFKQAEKPTRNIKE----DKKLLLETKITEVLSRLSIEPSEE----LEQE         509
         .*.*.***  *..*..** .* .** .* .**..** .*.*..*.*  **       *..

VgaB     YKLKLKELKSLNKNI                                                      552
Vga      FQNLINEKRNLDK--                                                      522
         ..  . *.. * *

PCR PRIMERS vatC

Oligo III     5'-atgaattcgcaaatcagcaagg-3'     SEQ ID NO: 19
                   EcoRI Oligo IV      5'-tcgtctcgagctctaggtcc-3'       SEQ ID NO: 20
                       SacI

FIG. 6A vgbB

Oligo V       5'-cagcagtctagatcagagtgg-3'      SEQ ID NO: 21
                       XbaI Oligo VI      5'-catacggatccaccttttcc-3'       SEQ ID NO: 22
                      BamHI

FIG. 6B vgaB

Oligo I       5'-AAGTCGACTGACAATATGAGTGGTGG-3'      SEQ ID NO:17

Oligo II      5'-CTGCAGATGCCTCAACAGCATCGATATCC-3'   SEQ ID NO: 18

FIG. 6C

SEQ ID NO: 1

*Seq vgaB*
ATGCTTAAAATCGACATGAAGAATGTAAAAAAATATTATGCAGATAAATTAATTTTAAATATAAA
AAAGATTTATAGTGGGGATAAAATAGGTATTGTAGGTAAGAATGGAGTTGGCAAAACAACACTTT
TAATAAAAGGACTAATAGAGATTGACGAAGGAAATATAATTATAAGTGAAAAAACAACTATTAAA
TCTCAATTAGAAGAACCACATAGTAAGATAATTGATGGAAAATATGCTTCAATATTTCAAGTTGA
GTGGAATGACAATATGAGTGGTGGTGAAAAAACTAGATTTAAACTAGCAGAGGGATTTCAAGATC
CTTTAATGCTCGTAGATGAACCTACAAGTAATTTAGATATCGAAGGAATAGAGTTGATAACAAAT
AAAGAGTACCGTGATACTTTTTTGGTAGTATCTCATGATAGAATTTTTTTAGATCAAGTTTGTAC
TTTTGAAATTGAAAATGGATATATTAGAGAATTCATCGGTAATTATACAAACTATATAGAGCAAA
TGCTTCTACGAAAGCAACAAGAAGAATACGAAAAGTATAATTCTAAAAGAAAGCAATTGGAGCAA
AAGCTAAAAGAGAATAAGGCGCAAGGAATGATTAAGCCCCCTTCAAAAACAATGGGAACATCTGA
AATATGGAAAATGCAACATGCTACTAAACAAAAAAAGATGCATAGAAATACGAATCGTTGGAAA
TAGATAAATTAAATCATGTAGAAAAAATAAAAGAGCTTCCTTCTATTAAAATGGATTTACCTAAT
CAATTTCATGGTCGCAATGTAATTAGTTTAAAAAACTTATCTATAAAATTTAATAATCAATTTCT
AGATGCTTCATTTGTCATTAAAGGTGGAGAAAAGGTTGCTATAATTGGTAACAATGGTGTAGGAA
CATTGTTGAAGCTGATTCTAGAAAAAGTAGAATCAGTAATAATATCACCATCAGTTAAAATTGGA
AGTCAAAACTTAGATGTTCTACAATCTCATAAATCTATCTTAGAAAATGTTATGTCTACCTCCAT
TGAAACAATAGCAAGAATTGTTCTAGCAAGATTACATTTTATCGCAATGATGTTCATAAAGAAA
TTTTGAGTGGTGGAGAACAAATAAAGGTTGCTTTTGCCAAGCTATTTGTTAGCGATTGTAATACA
CTTGATGAACCAACAAACTATTTGGATATCGATGCTGTTGAGGCATTAGAAGAATTGTTAATTAC
AGGTGTTGTGTTATTTGCTTCCCATGATAAAAAATTTATACAAAACCTAGCTGAACAATTGTTAA
AAAATAATAAAGTGAAAAAATTCGAAGGAACATATATAGAATATTTAAAAATTAAAGATAAACCA
AATACAAATGAAAAAGAACTCAAAGAAAAAAAGATGATACTAGAAATGCAAATTTCATCATTATT
AATCTCAATGGAAGAAAATGAAGAAAAAACAAAGAATTAGATGAAAAGTACAAATTGAAATTAA
TGAAAAGCCTAAATAAAAATATT

SEQ ID NO: 3

*Seq vgbB*
ATGAATTTTTATTTAGAGGAGTTTAACTTGTCTATTCCCGATTCAGGTCCATACGGTATAACTTC
AGACGGAAAGGTATGGTTCACACAACATAAGGCAAACAAAATCAGCAGTCTAGATCAGAGTGGTA
AAGAATTCGAAGTTCCTACCCCTGATGCTAAAGTGATGTGTTTAATTGTATCTTCACTTGGAGAC
TTTACAGAGAATGGTGCAAATAAAATCGGAAAGCTCTCAAAAAAAGGTGGCTTTACAGAATATCC
ACAGCCGGATTCTGGTCCTTACGGAATAACGGAAGGTCTAAATGGCGATATATGGTTTACCCAAT
GAGATCGTATAGGAAAGTTGACAGCTGATGGGACTATTTATGAATATGATTTGCCAAATAAGGGA
CCTGCTTTTATTACTTTAGGTTCGGATAACGCACTTTGGTTCACGGAGAACCAAAATAATTCTAT
GATTACAAATACAGGGAAATTAGAAGAATATCCTCTACCAACAAATGCAGCGGCTCCAGTGGGTA
GTGGTAACGATGGTGCACTCTGGTTTGTCGAATTATGGGCAACAAAATAGGTCGAATCACTACA
GAGATTAGCGAATATGATATTCCAACTCCAAACGCACGTCCACACGCTATAACCGCGGGGAAAAA
AATATGGTTTACTGAATGGGGGGCAAATCAAATCGGCAGAATTACAAACGACAAAACAATTCAAG
AACTTCAAACAGAAATGCGGAACCTCATGGTATTACCTTTGGAAAAGATGGATCCGTATGGTTT
AAATGTAAAATTGGGAAGCTGAATTTGAACGAA

FIG. 7A

SEQ ID NO: 2

SEQ vatC
ATGAAATGGCAAAATCAGCAAGGCCCCAATCCAGAAGAAATATACCCTATAGAAGGTAATAAAC
AATTTATTAAACCATCTATAACAAAGCCCAATATTTTAGTTGGGGAATATTCATATTACGATAG
TGGTGAATCTTTTGAAAGCCAAGTTCTTTATCACTATGAATTGATTGGGGATAAACTAATATTA
TTTTGTTCTATTGGACCCGGAACGACATTTATAATGAATGGGGCTAATCATCGTATGGATGGTT
TTCCATTCAATCTTTTCGGAAATGGTTGGGAGAAGCATACCCCTACATTGGAAGACCTTCCTTA
TAACACGGAAATTGGGAACGATGTTTGGATTGGACGAGATGTGACAATTATGCCCGGTGTAAAA
AACGGGGCTATTATTGCAGCAAAATCGGTTGTGACAAAGAACGTTGATCCTTATTCAGTTGTTG
ATCCTTCACGATTAATTAAGATAAGGTTTTCCAAGGAAAAAATCGCAGCATTACTAAAAGTAAG
GGACCTAGAGATAGAGACGATAAATGAAATATTGATTGCATCCTGAATGGTGATATAAAAAAG
AGAAGT

FIG. 7B

SEQ ID NO: 4

VgaB

MLKIDMKNVKKYYADKLILNIKELKIYSGDKIGIVGKNGVGKTTLLKIIK
GLIEIDEGNIIISHKTTIKYISQLEEPHSKIIDGKYASIFQVENKWNDNM
SGGEKTRFKLAEGFQDQCSLMLVDEPTSNLDIEGIELITNTFKEYRDTFL
VVSHDRIFLDQVCTKIFEIENGYIREFIGNYTNYIEQKEMLLRKQQEEYE
KYNSKRKQLEQAIKLKENKAQGMIKPPSKTMGTSESRIWKMQHATKQKKM
HRNTKSLETRIDKLNHVEKIKELPSIKMDLPNREQFHGRNVISLKNLSIK
FNNQFLWRDASFVIKGGEKVAIIGNNGVGKTTLLKLILEKVESVIISPSV
KIGYVSQNLDVLQSHKSILENVMSTSIQDETIARIVLARLHFYRNDVHKE
INVLSGGEQIKVAPAKLPVSDCNTLILDEPTNYLDIDAVEALEELLITYE
GVVLFASHDKKPIQNLAEQLLIIENNKVKKFEGTYIEYLKIKDKPKLNTN
EKELKEKKMILEMQISSLLSKISMEENEEKNKGLDEKYKLKLKELKSLNK
NI

SEQ ID NO: 6

VgbB

MNFYLEEFNLSIPDSGPYGITSSEDGKVWFTQHKANKISSLDQSGRIKEF
EVPTPDAKVMCLIVSSLGDIWFTENGANKIGKLSKKGGFTEYPLPQPDSG
PGITEGLNGDIWFTQLNGDRIGKLTADGTIYEYDLPNKGSYPAFITLGSD
NALWFTENQNNSIGRITNTGKLEEYPLPTNAAAPVGITSGNDGALWFVEI
MGNKIGRITTTGEISEYDIPTPNARPHAITAGKNSEIWFTEWGANQIGRI
TNDKTIQEYQLQTENAEPHGITFGKDGSVWFALKCKIGKLNLNE

SEQ ID NO: 5

VatC

MKWQNQQGPNPEEIYPIEGNKHVQFIKPSITKPNILVGEYSYYDSKDGES
FESQVLYHYELIGDKLILGKFCSIGPGTTFIMNGANHRMDGSTFPFNLFG
NGWEKHTPTLEDLPYKGNTEIGNDVWIGRDVTIMPGVKIGNGAIIAAKSV
VTKNVDPYSVVGGNPSRLIKIRFSKEKIAALLKVRWWDLEIETINENIDC
ILNGDIKKVKRS

FIG. 7C

```
SEQ ID NO: 7            K   S   I   L   E   N   V                    VgaB
                     1795                        1815
SEQ ID NO: 11       5' - aaa tct atc tta gaa aat gtt -3'              vgaB
                         g   agc t SEQ ID NO: 8            N   Y   T   N   Y   I   E   Q   K   E        VgaB
                                S           V
                     1237                                    1266
SEQ ID NO: 12       5' - aat tat aca aac tat ata gag caa aaa gaa -3' vgaB
                                 gt          gtt  a SEQ ID NO: 9            I   M   N   G   A   N   H   R   M            VatC
                     1187           a   c       a a          1213
SEQ ID NO: 13       5' - ata atg aat ggg gct aat cat cgt atg -3'      vatC
                         t           t   a   c       g SEQ ID NO: 10           G   N   D   V   W   I   G
                                                                      VatC
                     1310 a   t       g       t 1330
SEQ ID NO: 14       5' - ggg aac gat gtt tgg att gga - 3'             vatC
                             a   t       a       a t
```

FIG. 7D

KITS FOR USE IN DETECTING RESISTANCE TO STREPTOGRAMIN A AND RELATED COMPOUNDS

This application is a continuation application of U.S. application Ser. No. 09/446,301, filed Dec. 20, 1999 (now U.S. Pat. No. 6,506,893 B1), which is a National Stage application of PCT/IB98/00962, filed Jun. 22, 1998, which claims the benefit of U.S. Provisional Application No. 60/050,380, filed Jun. 20, 1997, the disclosures of each of which are hereby incorporated in their entireties by reference.

The present invention pertains to polynucleotides derived from *staphylococcal* genes encoding resistance to streptogramin A or to streptogramin B and chemically related compounds. This invention also relates to the use of the polynucleotides as oligonucleotide primers or probes for detecting *Staphylococcal* strains that are resistant to streptogramin A or to streptogramin B and related compounds in a biological sample.

In another embodiment, the present invention is directed to the full length coding sequences of the *staphylococcal* genes encoding for resistance to streptogramin A or to streptogramin B from *Staphylococcus* and to the polypeptides expressed by these full length coding sequences.

Further, this invention relates to the use of the expressed polypeptides to produce specific monoclonal or polyclonal antibodies that serve as detection means in order to characterize any *slaphylococcal* strain carrying genes encoding resistance to streptogramin A or to streptogramin B.

The present invention is also directed to diagnostic methods for detecting specific strains of *Staphylococcus* expected to be contained in a biological sample. The diagnostic methods use the oligonucleotide probes and primers as well as the antibodies of the invention.

Streptogramins and related compounds (antibiotics) produced by streptomycetes can be classified as A and B compounds according to their basic primary structures (Cocito, 1979). Compounds of the A group, including streptogramin A (SgA), pristinamycin IIA (PIIA), virginiamycin M, mikamycin A, or synergistin A, are polyunsaturated cyclic macrolactones. Compounds of the B group, including streptogramin B (SgB), pristinamycin B (PIB), virginiamycin S, mikamycin B, and synergistin B, are cyclic peptidic macrolactones (Cocito, 1979). Compounds of both groups, A and B, bind different targets in the peptidyltransferase domain of the 50S ribosomal subunit and inhibit protein elongation at different steps (Aumercier et al., 1992, Di Giambattista et al., 1989).

A decrease in the dissociation constant of PIB is observed in the presence of PIIA because this latter antibiotic provokes a conformational modification of the bacterial ribosome at the binding sites of these molecules. Thus, A and B compounds, which are bacteriostatic when used separately, act synergistically when combined and become bactericidal, mainly against Gram-positive bacteria.

Natural mixtures such as pristinamycin (Pt), synergistin, virginiamycin and mikamycin, are used orally and topically. A semi-synthetic injectable streptogramin, RP59500, consisting of a mixture of derivatives of A and B compounds (Dalfopristin and Quinupristin, respectively) is currently undergoing in vivo experimental and clinical trials (J. Antimicrob. Agents Chemother. 30 (Suppl. A), entire volume, 1992; Entenza et al., 1995, Fantin et al., 1995; Griswold et al., 1996; Torralba et al., 1995). *Staphylococcal* resistance to synergistic mixtures of A and B compounds (Pt MIC≧2 µg/ml) is always associated with resistance to A compounds (PIIA MIC≧8 µml), but not necessarily with resistance to B compounds (Allignet et al., 1996).

To date, four genes encoding resistance to A compounds have been isolated from staphylococcal and enterococcal plasmids. The genes vat (Allignet et al., 1993), vatB (Allignet and El Solh, 1995), and satA (Rende-Fournier et al., 1993) encode related acetyltransferases (50.4–58.3% amino acids), which inactivate streptogramin A and similar compounds. The staphylococcal gene vga (Allignet et al., 1992) encodes an ATP-binding protein probably involved in the active efflux of A compounds. Nevertheless, there continues to exist a need in the art for polynucleotides specific for *Staphylococcus* resistant to streptogramin A and/or B and related compounds.

SUMMARY OF THE INVENTION

Accordingly, this invention aids in fulfilling this need in the art. In particular, this invention provides a purified peptide comprising an amino acid sequence selected from the group consisting of:
 a) SEQ ID NO: 4 which corresponds to the complete amino acid sequence of Vga B or fragments derived from SEQ ID NO: 4 containing at least 10 amino acids;
 b) SEQ ID NO: 5 which corresponds to the complete amino acid sequence of Vat C or fragments derived from SEQ ID NO: 5 containing at least 10 amino acids;
 c) SEQ ID NO: 6 which corresponds to the complete amino acid sequence of Vgb B or fragments derived from SEQ ID NO. 6 containing at least 10 amino acids;
 d) SEQ ID NO: 7 which corresponds to the complete amino acid sequence of Vgb B;
 e) SEQ ID NO: 8 which corresponds to a fragment of the amino acid sequence of Vga B;
 f) SEQ ID NO: 9 which corresponds to a fragment of the amino acid sequence of Vat C; and
 g) SEQ ID NO: 10 which corresponds to a fragment of the amino acid sequence of Vat C.

This invention additionally provides a purified polynucleotide comprising the nucleotide sequence selected from the group consisting of:
 a) SEQ ID NO: 1 which corresponds to the complete nucleic acid sequence of vga B or fragments derived from SEQ ID NO: I containing 15 to 40 nucleotides;
 b) SEQ ID NO: 2 which corresponds to the complete nucleic acid sequence of vat C or fragments derived from SEQ ID NO: 2 containing 15 to 40 nucleotides;
 c) SEQ ID NO: 3 which corresponds to the complete nucleic acid sequence of vgb B or fragments derived from SEQ ID NO: 3 containing 15 to 40 nucleotides;
 d) SEQ ID NO: 11 which corresponds to the nucleic acid sequence encoding the polypeptide of SEQ ID NO: 7;
 e) SEQ ID NO: 12 which corresponds to the nucleic acid sequence encoding the polypeptide of SEQ ID NO: 8
 f) SEQ ID NO: 13 which corresponds to the nucleic acid sequence encoding the polypeptide of SEQ ID NO: 9; and
 g) SEQ ID NO: 14 which corresponds to the nucleic acid sequence encoding the polypeptide of SEQ ID NO: 10.

Furthermore, this invention includes a purified peptide comprising the amino acid sequence encoded by the nucleotide sequence selected from the group consisting of:
 a) SEQ ID NO: 1,
 b) SEQ ID NO: 2,
 c) SEQ ID NO: 3,
 d) SEQ ID NO: 11,
 e) SEQ ID NO: 12, f) SEQ ID NO: 13, and g) SEQ ID NO: 14.

This invention also provides a composition comprising purified polynucleotide sequences including at least one nucleotide sequence selected from the group consisting of polynucleotides, genes or cDNA of vgaB, vatC, and vgbB, which are useful for the detection of resistance to streptogramin A and/or to streptogramin B and related compounds. This invention further provides a composition comprising purified amino acid sequences including at least an amino acid sequence from a polypeptide encoded by a polynucleotide selected from the group consisting of polynucleotides, genes or cDNA of vgaB, vatC, and vgbB, which are useful for the detection of resistance to streptogramin A and/or to streptogramin B and related compounds.

In another embodiment, this invention provides a composition of polynucleotide sequences encoding resistance to streptogramins and related compounds, or inducing this resistance in Gram-positive bacteria, wherein the composition comprises a combination of at least two of the following nucleotide sequences: a) a nucleotide sequence encoding an acetyltransferase conferring resistance to streptogramin A and related compounds, b) a nucleotide sequence encoding a molecule containing ATP binding motifs conferring resistance to streptogramin A and related compounds; and c) a nucleotide sequence encoding a lactonase conferring resistance to streptogramin B and related compounds.

Furthermore, this invention provides a composition of polynucleotide sequences, wherein the sequence encoding a molecule containing ATP binding motifs confers resistance to Staphylococci and particularly to *S. aureus,* and wherein the polynucleotide sequence corresponds to a vgaB nucleotide sequence represented by SEQ ID NO: 1 or a sequence having at least 70% homology with vgaB complete nucleotide sequence, or to a polynucleotide hybridizing with SEQ ID NO: 1 under stringent conditions, or to a fragment containing between 20 and 30 nucleotides of SEQ ID NO: 11 or SEQ ID NO: 12, or wherein the polynucleotide sequence encodes a polypeptide having at least 60% homology with the complete SEQ ID NO: 4 or with SEQ ID NO: 7 or SEQ ID NO: 8.

Furthermore this invention relates to a composition of polynucleotide sequences, wherein the sequence encoding an acetyltransferase confers resistance to streptogramin A and related compounds in Staphylococci, and particularly in *S. cohnii,* and wherein the polynucleotide sequence corresponds to a vatC nucleotide sequence represented by SEQ ID NO: 2 or a sequence having at least 70% homology with vatC complete nucleotide sequence, or to a polynucleotide hybridizing with SEQ ID NO: 2 under stringent conditions, or to a fragment containing between 20 and 30 nucleotides of SEQ ID NO: 13 or SEQ ID NO: 14, or wherein the polynucleotide sequence encodes a polypeptide having at least 60% homology with the complete SEQ ID NO: 5 or with SEQ ID NO: 9 or SEQ ID NO: 10.

This invention also provides a composition of polynucleotide sequences, wherein the sequence encoding a lactonase confers resistance to streptogramin B and related compounds in Staphylococci and particularly in *S. cohnii,* and wherein the polynucleotide sequence corresponds to a vgbB nucleotide sequence represented in SEQ ID NO: 3 or a sequence having at least 70% homology with vgbB complete nucleotide sequence, or to a polynucleotide hybridizing with SEQ ID NO: 3 under stringent conditions, or to a fragment containing between 20 and 40 nucleotides of SEQ ID NO: 3, or wherein the polynucleotide sequence encodes a polypeptide having at least 60% homology with the complete SEQ ID NO: 6.

The invention also contemplates a composition of polynucleotide sequences, wherein at least a vatB nucleotide sequence encoding an acetyltransferase conferring resistance to streptogramin A and related compounds is included in addition to a vgaB nucleotide sequence encoding a molecule containing ATP binding motifs conferring resistance to streptogramin A.

Additionally, the invention includes a purified polynucleotide that hybridizes specifically under stringent conditions with a polynucleotide sequence selected from the group consisting of SEQ ID NO: 1, SEQ ID NO: 2, SEQ ID NO: 3, SEQ ID NO: 11, SEQ ID NO: 12, SEQ ID NO: 13, and SEQ ID NO: 14.

The invention further includes polynucleotide fragments comprising at least 10 nucleotides capable of hybridization under stringent conditions with any one of the nucleotide sequences enumerated above.

In another embodiment of the invention, a recombinant DNA sequence comprising at least one nucleotide sequence enumerated above and under the control of regulatory elements that regulate the expression of resistance to antibiotics of the streptogramin family in a defined host is provided.

Furthermore, the invention includes a recombinant vector comprising the recombinant DNA sequence noted above, wherein the vector comprises the plasmid pIP1633 or plasmid pIP1714.

The invention also includes a recombinant cell host comprising a polynucleotide sequence enumerated above or the recombinant vector defined above.

In still a further embodiment of the invention, a method of detecting bacterial strains that contain the polynucleotide sequences set forth above is provided.

Additionally, the invention includes kits for the detection of the presence of bacterial strains that contain the polynucleotide sequences set forth above.

The invention also contemplates antibodies recognizing peptide fragments or polypeptides encoded by the polynucleotide sequences enumerated above.

Still further, the invention provides for a screening method for active antibiotics and/or molecules for the treatment of infections due to Gram-positive bacteria, particularly staphylococci, based on the detection of activity of these antibiotics and/or molecules on bacteria having the resistance phenotype to streptogramins.

It is to be understood that both the foregoing general description and the following detailed description are exemplary and explanatory only and are not restrictive of the invention, as claimed.

BRIEF DESCRIPTION OF THE DRAWINGS

This invention will be more fully described with reference to the drawings in which.

FIG. 2 is the nucleotide sequence and deduced amino acid sequence of 2411 nucleotides from pIP1633, which contains the gene vgaB of *S. aureus* conferring resistance to streptogramin A and related compounds. The putative ribosome binding site (RBS) is underlined. The amino acids are aligned with the second nucleotide of each codon. Asterisks indicate the in-frame stop codons. The A and B ATP-binding motifs described by Walker et al. (1982) and detected within each of the two ATP-domains are boxed. The conserved motif SGG of the two copies of loop 3 described by Hyde et al. (1990) is underlined. Relevant restriction sites are shown.

FIG. 3 is the amino acid sequence alignment of the predicted 60 and 61 kDa proteins encoded by Vga (Allignet et al., 1992, accession No: m90056) and VgaB (FIG. 2), respectively. Identical residues are indicated by asterisks and conservative changes are shown by single dots. The A and B motifs of Walker et al. (1982) are in bold type (WA, WB) The conserved motif SGG of the two copies of loop 3 described by Hyde et al. (1990) is underlined.

FIG. 5 is the nucleotide sequence and deduced amino acid sequence of 1727 nucleotide from pIP1714, which contains the gene vgbB and vatC of *S. cohnii*. Relevant restriction sites are shown.

FIGS. 6A, 6B, and 6C represent oligonucleotide primers for hybridization under stringent conditions with vatC, vgbB, and vgaB respectively.

FIG 7 represents SEQ ID NOs: 1–14.

DETAILED DESCRIPTION OF THE INVENTION

Figures 1A, 1B:
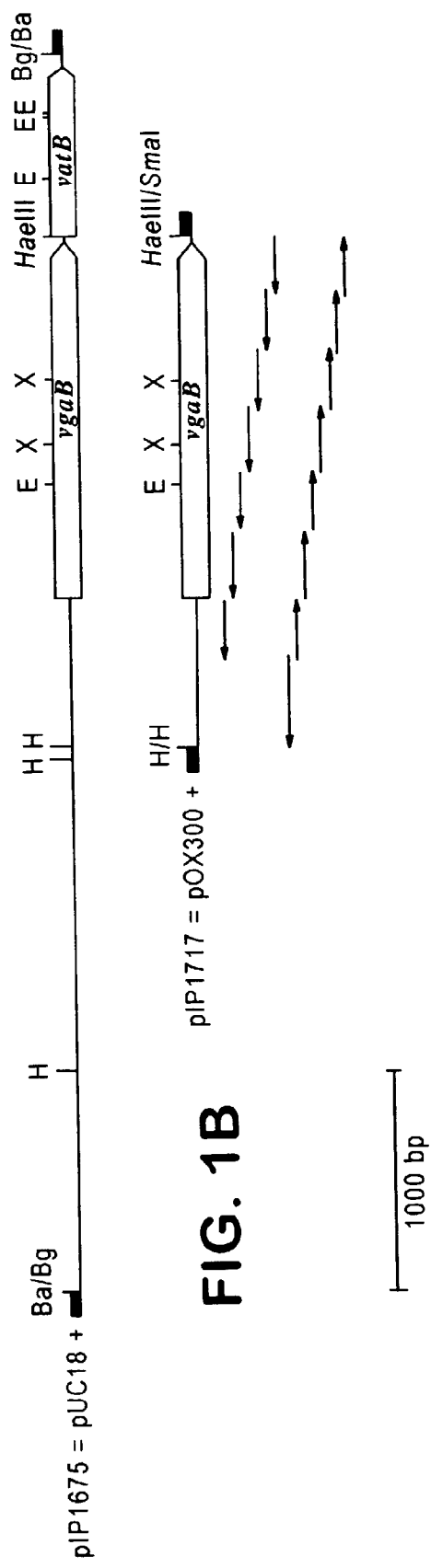
FIGS. 1A and 1B are the restriction maps of the 5.5 kb Bg/II fragment and of the 2.4 kb HindIII-HaeIII fragment of pIP1633, respectively. Both fragments confer resistance to streptogramin A and related compounds. The strategy for sequencing the 2–4 kb HindIII-HaeIII fragment is given in FIG. 1B. Restriction enzyme abbreviations: Ba, BamHI, Bg, Bg/II; E, EcoRI; H, HindIII, X, XbaI.

It has now been determined that bacteria from the *Staphylococcus* genus carry a vgaB gene, which encodes a putative ATP-binding protein that confers resistance to streptogramin A and structurally similar compounds. It has also now been determined that bacteria from the *Staphylococcus* genus carry a vgbB gene, which encodes a lactonase that confers resistance to streptogramin B and structurally similar compounds, and a vatC gene, which encodes an acetyltransferase that confers resistance to streptogramin A and structurally similar compounds.

Novel polynucleotides corresponding to the vgaB, vgbB, and vatC genes from various strains of *Staphylococcus* have been isolated and sequenced, and it has been surprisingly demonstrated that these new polynucleotides make it possible to design oligonucleotide probes or primers. These polynucleotides include the following:
a) SEQ ID NO: 1,
b) SEQ ID NO: 2,
c) SEQ ID NO: 3,
d) SEQ ID NO: 11,
e) SEQ ID NO: 12,
f) SEQ ID NO: 13, and
g) SEQ ID NO: 14.

This invention provides specific pairs of oligonucleotide primers or probes that hybridize specifically, under stringent hybridization conditions as defined hereinafter, to the nucleic acid (RNA or DNA) from a particular strain of the *Staphylococcus* genus. These oligonucleotide primers include the following:

a) Oligo I 5'-AAGTCGACTGACAATATGAGTGGTGG-3' (SEQ ID NO:17), and

-continued
Oligo II 5'-CTGCAGATGCCTCAACAGCATCGATATCC-3' (SEQ ID NO:18);

b) Oligo III 5'-ATGAATTCGCAAATCAGCAAGG-3' (SEQ ID NO:19), and

Oligo IV 5'-TCGTCTCGAGCTCTAGGTCC-3' (SEQ ID NO:20); and c) Oligo V 5'-CAGCAGTCTAGATCAGAGTGG-3' (SEQ ID NO:21), and Oligo VI 5'-CATACGGATCCACCTTTTCC-3' (SEQ ID NO:22).

In a specific embodiment of the present invention, the purified polynucleotides useful for detecting Staphylococcal strains can be used in combination in order to detect bacteria belonging to Staphylococci in a biological sample Thus, the present invention also provides detection methods and kits comprising combinations of the purified polynucleotides according to the invention The purified oligonucleotides of the invention are also useful as primers for use in amplification reactions or as nucleic acid probes.

By "polynucleotides" according to the invention is meant the sequences referred to as SEQ ID NOs: 1, 2, 3, OR 11, 12, 13, 14 and the complementary sequences and/or the sequences of polynucleotides which hybridize to the referred sequences in high stringent conditions and which are used for detecting *staphylococcal* strains carrying a gene encoding resistance to streptogramin A or to streptogramin B.

By "active molecule" according to the invention is meant a molecule capable of inhibiting the activity of the purified polypeptide as defined in the present invention or capable of inhibiting the bacterial culture of *staphylococcal* strains.

Thus, the polynucleotides of SEQ ID NOs: 1–3 and 11–14 and their fragments can be used to select nucleotide primers notably for an amplification reaction, such as the amplification reactions further described.

PCR is described in the U.S. Pat. No. 4,683,202 granted to Cetus Corp. The amplified fragments may be identified by agarose or polyacrylamide gel electrophoresis, or by a capillary electrophoresis, or alternatively by a chromatography technique (gel filtration, hydrophobic chromatography, or ion exchange chromatography). The specificity of the amplification can be ensured by a molecular hybridization using as nucleic probes the polynucleotides of SEQ ID NOs: 1–3 and 11–14 and their fragments, oligonucleotides that are complementary to these polynucleotides or fragments thereof, or their amplification products themselves.

Amplified nucleotide fragments are useful as probes in hybridization reactions in order to detect the presence of one polynucleotide according to the present invention or in order to detect the presence of a bacteria of *Staphylococcal* strain carrying genes encoding resistance to streptogramin A or streptogramin B, in a biological sample. This invention also provides the amplified nucleic acid fragments ("amplicons") defined herein above. These probes and amplicons can be radioactively or non-radioactively labeled, using for example enzymes or fluorescent compounds.

Preferred nucleic acid fragments that can serve as primers according to the present invention are the following:
polynucleotides of sequence SEQ ID NOs: 1–3 and 11–14; and
polynucleotides having a length from 20 to 30 consecutive nucleotides from a polynucleotide selected from the group consisting of polynucleotides of sequences SEQ ID NO: 11 to SEQ ID NO: 14 or from 20 to 40 consecutive nucleotides from a polynucleotide of SEQ ID NO: 3.

The primers can also be used as oligonucleotide probes to specifically detect a polynucleotide according to the invention.

Other techniques related to nucleic acid amplification can also be used and are generally preferred to the PCR technique. The Strand Displacement Amplification (SDA) technique (Walker et al., 1992) is an isothermal amplification technique based on the ability of a restriction enzyme to cleave one of the strands at a recognition site (which is under a hemiphosphorothioate form), and on the property of a DNA polymerase to initiate the synthesis of a new strand from the 3' OH end generated by the restriction enzyme and on the property of this DNA polymerase to displace the previously synthesized strand being localized downstream.

The SDA amplification technique is more easily performed than PCR (a single thermostated water bath device is necessary), and is faster than the other amplification methods. Thus, the present invention also comprises using the nucleic acid fragments according to the invention (primers) in a method of DNA or RNA amplification according to the SDA technique. The polynucleotides of SEQ ID NOs: 1–3 and 11–14 and their fragments, especially the primers according to the invention, are useful as technical means for performing different target nucleic acid amplification methods such as:

TAS (Transcription-based Amplification System), described by Kwoh et al. in 1989;

SR (Self-Sustained Sequence Replication), described by Guatelli et al. in 1990,

NASBA (Nucleic acid Sequence Based Amplification), described by Kievitis et al. in 1991; and TMA (Transcription Mediated Amplification).

The polynucleotides of SEQ ID NOs: 1–3 and 11–14 and their fragments, especially the primers according to the invention, are also useful as technical means for performing methods for amplification or modification of a nucleic acid used as a probe, such as:

LCR (Ligase Chain Reaction), described by Landegren et al. in 1985 and improved by Barany et al. in 1991, who employ a thermostable ligase;

RCR (Repair Chain Reaction), described by Segev et al. in 1992;

CPR (Cycling Probe Reaction), described by Duck et al. in 1990; and

Q-beta replicase reaction, described by Miele et al. in 1983 and improved by Chu et al. in 1986, Lizardi et al. in 1988, and by Burg et al. and Stone et al. in 1996.

When the target polynucleotide to be detected is RNA, for example mRNA, a reverse transcriptase enzyme can be used before the amplification reaction in order to obtain a cDNA from the RNA contained in the biological sample. The generated cDNA can be subsequently used as the nucleic acid target for the primers or the probes used in an amplification process or a detection process according to the present invention.

Nucleic probes according to the present invention are specific to detect a polynucleotide of the invention. By "specific probes" according to the invention is meant any oligonucleotide that hybridizes with one polynucleotide of SEQ ID NOs: 1–3 and 11–14 and which does not hybridize with unrelated sequences. Preferred oligonucleotide probes according to the invention are oligonucleotides I–VI.

In a specific embodiment, the purified polynucleotides according to the present invention encompass polynucleotides having at least 80% homology in their nucleic acid sequences with polynucleotides of SEQ ID NO: 11 to SEQ ID NO: 14, at least 70% identity with SEQ ID NO: 1 to 3. By percentage of nucleotide homology according to the present invention is intended a percentage of identity between the corresponding bases of two homologous polynucleotides, this percentage of identity being purely statistical and the differences between two homologous polynucleotides being located at random and on the whole length of said polynucleotides.

The oligonucleotide probes according to the present invention hybridize specifically with a DNA or RNA molecule comprising all or part of one polynucleotide among SEQ ID NOs: 1–3 and 11–14 under stringent conditions. As an illustrative embodiment, the stringent hybridization conditions used in order to specifically detect a polynucleotide according to the present invention are advantageously the following:

Prehybridization and hybridization are performed at 68° C. in a mixture containing:

5×SSPE (1×SSPE is 0.3 M NaCl, 30 mM tri-sodium citrate

5× Denhardt's solution 0.5% (w/v) sodium dodecyl sulfate (SDS); and

100 μg ml$^{-1}$ salmon sperm DNA

The washings are performed as follows:

Two washings at laboratory temperature for 10 min. in the presence of 2×SSPE and 0.1% SDS;

One washing at 68° C. for 15 min. in the presence of 1×SSPE, 0.1% SDS; and

One washing at 68° C. for 15 min in the presence of 0.1×SSPE and 0.1% SDS.

The non-labeled polynucleotides or oligonucleotides of the invention can be directly used as probes. Nevertheless, the polynucleotides or oligonucleotides are generally labeled with a radioactive element ($^{32}$P, $^{35}$S, $^{3}$H, $^{125}$I) or by a non-isotopic molecule (for example, biotin, acetylaminofluorene, digoxigenin, 5-bromodesoxyuridin, fluorescein) in order to generate probes that are useful for numerous applications. Examples of non-radioactive labeling of nucleic acid fragments are described in the French Patent No FR 78 10975 or by Urdea et al. or Sanchez-Pescador et al. 1989. WO 98/59058 PCT/IB98/00962

Other labeling techniques can also be used, such as those described in the French patents 2 422 956 and 2 518 755. The hybridization step may be performed in different ways (Matthews et al. 1988). A general method comprises immobilizing the nucleic acid that has been extracted from the biological sample on a substrate (nitrocellulose, nylon, polystyrene) and then incubating, in defined conditions, the target nucleic acid with the probe. Subsequent to the hybridization step, the excess amount of the specific probe is discarded, and the hybrid molecules formed are detected by an appropriate method (radioactivity, fluorescence, or enzyme activity measurement).

Advantageously, the probes according to the present invention can have structural characteristics such that they allow signal amplification, such structural characteristics being, for example, branched DNA probes as those described by Urdea et al. in 1991 or in the European Patent No. 0 225 807 (Chiron).

In another advantageous embodiment of the present invention, the probes described herein can be used as "capture probes", and are for this purpose immobilized on a substrate in order to capture the target nucleic acid contained in a biological sample.

The captured target nucleic acid is subsequently detected with a second probe, which recognizes a sequence of the target nucleic acid that is different from the sequence recognized by the capture probe.

The oligonucleotide fragments useful as probes or primers according to the present invention can be prepared by cleavage of the polynucleotides of SEQ ID NOs: 1–3 and 11–14 by restriction enzymes, as described in Sambrook et al. in 1989. Another appropriate preparation process of the nucleic acids of the invention containing at most 200 nucleotides (or 200 bp if these molecules are double-stranded) comprises the following steps:

synthesizing DNA using the automated method of beta-cyanethylphosphoramidite described in 1986;
cloning the thus obtained nucleic acids in an appropriate vector; and
purifying the nucleic acid by hybridizing to an appropriate probe according to the present invention.

A chemical method for producing the nucleic acids according to the invention, which have a length of more than 200 nucleotides (or 200 bp if these molecules are double-stranded), comprises the following steps:

Assembling the chemically synthesized oligonucleotides having different restriction sites at each end;
cloning the thus obtained nucleic acids in an appropriate vector; and
purifying the nucleic acid by hybridizing to an appropriate probe according to the present invention.

The oligonucleotide probes according to the present invention can also be used in a detection device comprising a matrix library of probes immobilized on a substrate, the sequence of each probe of a given length being localized in a shift of one or several bases, one from the other, each probe of the matrix library thus being complementary to a distinct sequence of the target nucleic acid. Optionally, the substrate of the matrix can be a material able to act as an electron donor, the detection of the matrix positions in which hybridization has occurred being subsequently determined by an electronic device. Such matrix libraries of probes and methods of specific detection of a target nucleic acid are described in the European patent application No. 0 713 016, or PCT Application No. WO 95 33846, or also PCT Application No. WO 95 11995 (Affymax Technologies), PCT Application No. WO 97 02357 (Affymetrix Inc.), and also in U.S. Pat. No. 5,202,231 (Drmanac), said patents and patent applications being herein incorporated by reference.

The present invention also pertains to a family of recombinant plasmids containing at least a nucleic acid according to the invention According to an advantageous embodiment, a recombinant plasmid comprises a polynucleotide of SEQ ID NOs: 1–3 and 11–14 or one nucleic fragment thereof. More specifically, the following plasmids are part of the invention: pIP163 and pIP1714.

The present invention is also directed to the full length coding sequences of the vgaB, vgbB, and vatC genes from Staphylococci that are available using the purified polynucleotides according to the present invention, as well as to the polypeptide enzymes encoded by these full length coding sequences. In a specific embodiment of the present invention, the full length coding sequences of the vgaB, vgbB, and vatC genes are isolated from a plasmid or cosmid library of the genome of Staphylococci that have been screened with the oligonucleotide probes according to the present invention. The selected positive plasmid or cosmid clones hybridizing with the oligonucleotide probes of the invention are then sequenced in order to characterize the corresponding full length coding sequence, and the DNA insert of interest is then cloned in an expression vector in order to produce the corresponding ATP binding motif conferring resistance to streptogramin A and related compounds, acetyltransferase conferring resistance to streptogramin A and related compounds, or lactonase conferring resistance to streptogramin B and related compounds.

A suitable vector for the expression in bacteria and in particular in *E. Coli*, is the pQE-30 vector (QIAexpress) that allows the production of a recombinant protein containing a 6xHis affinity tag The 6xHis tag is placed at the C-terminus of the recombinant polypeptide ATP binding motif conferring resistance to streptogramin A and related compounds, acetyltransferase conferring resistance to streptogramin A and related compounds or lactonase conferring resistance to streptogramin B and related compounds, which allows a subsequent efficient purification of the recombinant polypeptide ATP binding motif conferring resistance to streptogramin A and related compounds, acetyltransferase conferring resistance to streptogramin A and related compounds, or lactonase conferring resistance to streptogramin B and related compounds by passage onto a nickel or copper affinity chromatography column The nickel chromatography column can contain the Ni-NTA resin (Porath et al. 1975)

The polypeptides according to the invention can also be prepared by conventional methods of chemical synthesis, either in a homogenous solution or in solid phase. As an illustrative embodiment of such chemical polypeptide synthesis techniques the homogenous solution technique described by Houbenweyl in 1974 may be cited.

The polypeptides according to the invention can be characterized by binding onto an immunoaffinity chromatography column on which polyclonal or monoclonal antibodies directed to a polypeptide among the ATP binding motif conferring resistance to streptogramin A and related compounds, acetyltransferase conferring resistance to streptogramin A and related compounds, or lactonase conferring resistance to streptogramin B and related compounds of the invention have previously been immobilized.

Another object of the present invention comprises a polypeptide produced by the genetic engineering techniques or a polypeptide synthesized chemically as above described.

The polypeptide ATP binding motif conferring resistance to streptogramin A and related compounds, acetyltransferase conferring resistance to streptogramin A and related compounds, or lactonase conferring resistance to streptogramin B and related compounds according to the present invention are useful for the preparation of polygonal or monoclonal antibodies that recognize the polypeptides or fragments thereof. The monoclonal antibodies can be prepared from hybridomas according to the technique described by Kobler and Milstein in 1975. The polyclonal antibodies can be prepared by immunization of a mammal, especially a mouse or a rabbit, with a polypeptide according to the invention that is combined with an adjuvant, and then by purifying specific antibodies contained in the serum of the immunized animal on a affinity chromatography column on which has previously been immobilized the polypeptide that has been used as the antigen.

Consequently, the invention is also directed to a method for detecting specifically the presence of a polypeptide according to the invention in a biological sample. The method comprises:

a) bringing into contact the biological sample with an antibody according to the invention; and b) detecting antigen-antibody complex formed.

Also part of the invention is a diagnostic kit for in vitro detecting the presence of a polypeptide according to the present invention in a biological sample. The kit comprises:

a polyclonal or monoclonal antibody as described above, optionally labeled; and a reagent allowing the detection of the antigen-antibody complexes formed, wherein the reagent carries optionally a label, or being able to be recognized itself by a labeled reagent, more particularly in the case when the above-mentioned monoclonal or polyclonal antibody is not labeled by itself.

Indeed, the monoclonal or polyclonal antibodies according to the present invention are useful as detection means in order to identify or characterize a *Staphylococcal* strain carrying genes encoding resistance to streptogramin A or streptogramin B.

The invention also pertains to:

A purified polypeptide or a peptide fragment having at least 10 amino acids, which is recognized by antibodies directed against a polynucleotide sequence conferring resistance to streptogramin and related compounds, corresponding to a polynucleotide sequence according to the invention.

A polynucleotide comprising the full length coding sequence of a *Staphylococcus* streptogramin A and/or B resistant gene containing a polynucleotide sequence according to the invention.

A monoclonal or polyclonal antibody directed against a polypeptide or a peptide fragment encoded by the polynucleotide sequences according to the invention.

A method of detecting the presence of bacterium harboring the polynucleotide sequences according to the invention in a biological sample comprising:

a) contacting bacterial DNA of the biological sample with a primer or a probe according to the invention, which hybridizes with a nucleotide sequence encoding resistance to streptogramins;

b) amplifying the nucleotide sequence using said primer or said probe; and c) detecting the hybridized complex formed between said primer or probe with the DNA.

A kit for detecting the presence of bacterium having resistance to streptogramin A and/or streptogramin B and harboring the polynucleotide sequences according to the invention in a biological sample, said kit comprising:

a) a polynucleotide probe according to the invention; and b) reagents necessary to perform a nucleic acid hybridization reaction.

A kit for detecting the presence of bacterium having resistance to streptogramin A and harboring the polynucleotide sequences according to the invention in a biological sample, said kit comprising:

a) a polynucleotide probe according to the invention; and b) reagents necessary to perform a nucleic acid hybridization reaction.

A method of screening active antibiotics for the treatment of the infections due to Gram-positive bacteria, comprising the steps of:

a) bringing into contact a Gram-positive bacteria having a resistance to streptogramin A or streptogramin B and related compounds and containing the polynucleotide sequences according to the invention with the antibiotic; and b) measuring an activity of the antibiotic on the bacteria having a resistance to streptogramins and related compounds.

A method of screening for active synthetic molecules capable of penetrating into a bacteria of the family of staphylococci, wherein the inhibiting activity of these molecules is tested on at least a polypeptide encoded by the polynucleotide sequences according to the invention comprising the steps of:

a) contacting a sample of said active molecules with the bacteria;

b) testing the capacity of the active molecules to penetrate into the bacteria and the capacity of inhibiting a bacterial culture at various concentration of the molecules; and c) choosing the active molecule that provides an inhibitory effect of at least 80% on the bacterial culture compared to an untreated culture.

An in vitro method of screening for active molecules capable of inhibiting a polypeptide encoded by the polynucleotide sequences according to the invention, wherein the inhibiting activity of these molecules is tested on at least said polypeptide, said method comprising the steps of:

a) extracting a purified polypeptide according to the invention;

b) contacting the active molecules with said purified polypeptide;

c) testing the capacity of the active molecules, at various concentrations, to inhibit the activity of the purified polypeptide; and d) choosing the active molecule that provides an inhibitory effect of at least 80% on the activity of the said purified polypeptide.

A composition of a polynucleotide sequence encoding resistance to streptogramins and related compounds, or inducing resistance in Gram-positive bacteria, wherein said composition comprises a nucleotide sequence corresponding to the resistance phenotype of the plasmid pIP1633 deposited with the C.N.C.M. under the Accession No. I-1768 and of the plasmid pIP1680 deposited with the C.N.C.M. under the Accession No. I-1767 and of the plasmid pIP1714 deposited with the C.N.C.M. under the number I-1877 on Jun. 18, 1997.

A method of detecting the presence of bacterium harboring the polynucleotide sequences according to the invention in a biological sample, said method comprising the steps of:

a) contacting said sample with an antibody according to the invention that recognizes a polypeptide encoded by said polynucleotide sequences; and b) detecting said complex.

A diagnostic kit for iii vitro detecting the presence of bacterium harboring the polynucleotide sequences according to the invention in a biological sample, said kit comprising:

a) a predetermined quantity of monoclonal or polyclonal antibodies according to the invention;

b) reagents necessary to perform an immunological reaction between the antibodies and a polypeptide encoded by said polynucleotide sequences; and c) reagents necessary for detecting said complex between the antibodies and the polypeptide encoded by said polynucleotide sequences.

The inhibiting activity of the molecules can be readily evaluated by one skilled in the art. For example, the inhibiting activity of Vga B can be tested by detecting its ATP hydrolysis as described in J. I. Ross et al. (1990), Mol. Microbiol. 4(7):1207–1214 regarding the rate evaluation of the active efflux of antibiotics from a cell. Ross et al. use a different gene, but their gene product functions as a drug efflux pump in the same way as Vga B does.

The inhibiting activity of Vat C can be tested by visualizing the acetylation reaction as described in Allignet et al. (1993) regarding the mechanism of inactivation of A-type compounds conferred by plasmids pIP680 and pIP1156 by thick layer chromatography and NMR.

The inhibiting activity of Vgb B can be tested by detecting the degradation of streptogramin B or a related compound by a microbiological test as described in Allignet et al. (1988)

Plasmids containing the polynucleotides from Staphylococci, which confer streptogramin A and/or B resistance, are referred to herein by the following accession numbers:

| Plasmid | Accession No |
|---------|--------------|
| pIP1714 | I-1877 |
| pIP1633 | I-1768 |
| pIP680 | I-1767 | and they have been inserted into vectors which have been deposited at the Collection Nationale de Cultures de Microorganismes ("C.N.C.M.") Institut Pasteur, 28, rue du Docteur Roux, F-75724 Paris Cedex 15, France on Jun. 18, 1997, and Aug. 7, 1996, respectively.

EXAMPLES

Example 1

Cloning of the vgaB Gene Carried by Plasmid pIP1633 pIP1633 was isolated from a *S. aureus* transconjugant strain, BM12235, obtained from the donor wild-type *S. aureus strain*, BM3385 (Allignet and El Solh, 1995). This plasmid carried the vatB gene located on a 5.5 Bg/II fragment, but the other described streptogramin A resistant (SgA') genes were not detected either by hybridization experiments or by PCR (Allignet and El Solh, 1995). Since the gene vga was carried by all the tested staphylococcal plasmids containing the vat gene (Allignet et al., 1996), the presence of a vga-related gene was suspected in pIP1633. We therefore searched this gene in the recombinant plasmid, pIP1675 (FIG. 1A), containing the vatB-5.5 Bg/II fragment of pIP1633.

First, the 2.4 kb HindIII-HaeIII fragment of pIP1675, which contains only 10 nucleotide from vatB, was inserted into plasmid pOX300, and the recombinant plasmid, pIP1717 (FIG. 1B), was introduced by electroporation into the *S. aureus* recipient, RN4220 (Kreiswirth et al., 1983). Plasmid pOX300, also named pOX7, (Dyke and Curnock, 1989), is a hybrid of pUC18 and pE194ts and replicates in *E. coli* where it confers resistance to ampicillin and to erythromycin, and in *S. aureus* where only resistance to erythromycin is expressed. The *S. aureus* transformants selected on 10 μg/ml erythromycin were resistant to streptogramin A and related compounds (PIIA MICs =8–16 pig/ml). Thus, the 2.4-kb HindIII-HaeIII insert of pIP1717 (FIG. 1B) probably carried a streptogramin A resistance gene and was sequenced. The nucleotide (nucleotide) sequence of this fragment was determined by the dideoxy method (Sanger et al., 1977) with the reagents and the procedure recommended by the suppliers of the $T^7$ sequencing kit (Pharmacia International). Arrows indicate the direction and extent of each dideoxy-sequencing reaction. (FIG. 1B).

Example 2

The Nucleotide Sequence of the vgaB Gene

The strategy of sequencing on both strands is outlined in FIG. 1 and the sequence of the 2411-bp HindIII-HaeIII insert is given in FIG. 9. An open reading frame (ORF) of 1674 nucleotide extending from nucleotide 682 to 2356 was detected on the same strand as vatB (FIG. 2). The 1674 nucleotide ORF contained an ATG start codon at nucleotide 700 to 702 and was preceded by an 8 nucleotide putative RBS. The ΔG (free energy of association) of interaction of the most stable structure between this putative RBS and the 3'-terminus of the 165 rRNA (MacLaughlin et al., 1981; Moran et al., 1982) calculated according to Tinoco et al. (1973) was −79.4 kJ/mol. The sequence located between the ATG codon and the TAA stop codon at nucleotide 2356 to 2358 may encode a 552 amino acid protein of 61,327 daltons (Da). This putative gene, named vgaB, had 58.8% nucleotide identity with the 1572 bp gene, vga (Allignet et al., 1992). The G+C content of vgaB (27.2%) is similar to that of vga (29%), but both values are slightly lower than those of the staphylococcal genome (32 to 36%) (KIoos and Schleifer, 1986) The nucleotide sequence of vgaB has been submitted to the GenBank/EMBL data bank under accession no. u82085.

Example 3

Amino Acid Sequence Analysis of VgaB

The predicted translation product of the vgaB gene, VgaB, has a calculated isoelectric point (pI) of 9.60. The hydropathy plot of the VgaB sequence according to the algorithm of Kyte and Doolittle (1982) indicates the protein to be hydrophilic. No similarity to known signal sequences of secreted proteins (von Heijne, 1986; Watson, 1984) was observed.

The amino acid sequence of VgaB was compared with the sequences available in databases (GenBank, release 97.0, EMBL, release 48; SwissProt, release 34). Significant similarity to the ATP-binding domains of numerous ATP-binding Cassette (ABC) proteins was found The protein giving the best match was Vga (48.3% identical amino acid, 70.4% similar amino acid). VgaB and Vga each contain two ATP-binding domains sharing 38 8% and 39.1% identical amino acid, respectively Each of these domains includes the two ATP-binding motifs described by Walker et al. (1982) (FIG. 2). Moreover, the highly conserved SGG sequence of loop 3 found between the two ATP-binding motifs of all investigated ATP-binding proteins (Barrasa et al., 1995; Hyde et al., 1990) was detected in Vga (Allignet et al., 1992) and VgaB (FIG. 2). According to the predicted tertiary structure of ABC model cassette, this loop would be conveniently located to interact with the cell membrane (Hyde et al., 1990). The inter-ATP-binding domain of VgaB is more rich in glutamine (11 Q in 155 amino acid total) than the rest of the sequence of the protein (11 Q/397 amino acid) In contrast, the proportion of glutamine in the inter-ATP-binding domain of Vga is similar to that in the other part of the protein (4 Q/156 amino acid and 14 Q/366 amino acid, respectively). Neither Vga nor VgaB contains hydrophobic transmembrane domains.

The ABC protein MsrA (Ross et al., 1990) is the most similar to Vga and VgaB (35.2% and 34.4% identical amino acid, respectively). MsrA confers resistance to erythromycin by increasing the efflux of this antibiotic and to streptogramin B by a mechanism not yet elucidated. MsrA contains two ATP-binding domains with 31.8% amino acid identity and separated by a Q-linker, but no hydrophobic stretches that might be potential membrane spanning domains. The hydrophobic proteins, which are expected to interact with MsrA, are those encoded by similar genes mapping near MsrA in two staphylococcal strains (smpA, smpB) and also those on the chromosome of the *S. aureus* recipient strain, RN4220 (smpC), which does not carry msrA (Ross et al., 1995). Ross et al. (1996) have recently reported that SmpC found in the chromosome of RN4220 is not essential for the expression of resistance to erythromycin conferred by MsrA. Thus, further experiments are required to elucidate the mechanisms of resistance conferred by msrA, vga, or vgaB genes.

Several ABC transporters, which do not have alternating hydrophobic domains, have been Grouped in a subfamily in order to distinguish them from the members of the $ABC_2$ transporter subfamily, the members of which contain hydrophobic transmembrane domains (Barrasa et al., 1995; Olano et al, 1995; Peschke et al., 1995). Thus, VgaB may be considered as a new member of the former ABC transporter subfamily. Excluding VgaB, Vga, and MsrA, most of the known ABC transporters that contain two ATP-binding cassettes but no hydrophobic domain(s) were found in lantibiotic or antibiotic producing microorganisms in which they are involved in the active excretion of these molecules. These transporters are encoded by the following genes: ardl, an amino-acylnucleoside antibiotic resistance gene from *Streptomyces capreolus* (Barrasa et al., 1995); carA, a carbomycin-resistance gene from *Streptomyces thermotolerans* (Schoner et al., 1992); ImrC, a lincomycin-resistance gene from *Streptomyces lincolnensis* (Peschke et al., 1995); oleB, an oleandomycin-resistance gene from *Streptomyces antibioticus* (Olano et al., 1995); srmB, a spiramycin-resistance gene from *Streptomyces ambofaciens* (Geistlich et al., 1992); tirC, a tylosin-resistance gene from *Streptomyces fradiae* (Rosteck et al., 1991); and petT, a pep5 epidermin-resistance gene from *Staphylococcus epidermidis* (Meyer et al., 1995). The amino acid identity between each of these latter ABC transporters and VgaB is between 23.6% and 28.7%.

Degenerate primers designed from an analysis of the alignment of the amino acid sequence of Vga and VgaB may be helpful to detect such putative genes by PCR experiments. In the streptogramins producers, the described resistance to these antibiotics consists of streptogramin A inactivation by an as yet unknown mechanism (Fierro et al., 1989), streptogramin B inactivation by a lactonase (Kim et al., 1974) and putative increased export of streptogramin A and streptogramin B by an integral membrane protein, Ptr, exploiting transmembrane proton gradients (Blanc et al., 1995). The NMR spectra of the modified A compounds may be analyzed to verify if their inactivation in the antibiotic producers is similar to that due to the proteins Vat or VatB, which transfer an o-acetyl group to position C14 of PIIA (Allignet et al., 1993). Interestingly, the staphylococcal gene vgb (Allignet et al., 1988) found in most plasmids carrying vga and vat (Allignet et al., 1996), encodes a protein inactivating streptogramin B and related compounds by cleavage of the lactone ring.

Example 4

Distribution and Location of the vgaB Gene in 52 $SgA^R$ and Independent Wild-type Staphylococci A recombinant plasmid containing a fragment of vgaB, pIP1705, was constructed to serve as a probe in hybridization experiments under stringen conditions as described previously (Allignet et al., 1996). pIP1705 consists of pUC19 cleaved with Sa/I and PstI, and an insert of 1051 b amplified from within vgaB by the following primers, which introduce PstI or SalI sites:

```
                                          (SEQ ID NO:17)
Oligo I     5'-AAGTCGACTGACAATATGAGTGGTGG-3'
               SalI (SEQ ID NO:18)
Oligo II    5'-CTGCAGATGCCTCAACAGCATCGATATCC-3'
               PstI
```

The 52 SgA' staphylococci investigated (Allignet et al., 1996; El Solh et al., 1980, Loncle et al., 1993) included 10 strains (7 *S. aureus*, 1 *S. simulans*, 1 *S. haemolyticus*, and 1 *S. cohnii urealyticum*), which harbored 26 to 45 kb plasmids containing vga, vat, and vgb, 21 strains (20 *S. aureus* and one *S. epidermidis*), which harbored 50 to 90 kb plasmids containing vatB; 16 strains (12 *S. epidermidis*, three *S. haemolyticus* and one *S. aureus*) with 6 to 15 kb plasmids containing vga; one *S. epidermidis* strain which harbored a plasmid of approximately 20 kb containing vga-vat; and four *S. aureus* strains, which do not carry nucleotide sequences hybridizing with vat, vatB, vga, or vgb. Nucleotide sequences hybridizing with pIP1705 were found only in the 21 large plasmids containing vatB. In all these 21 plasmids including pIP1633, the hybridizing nucleotide sequences were detected on a 1.5 kb EcoRI fragment, which also hybridized with vatB, suggesting that vgaB and vatB have conserved relative positions.

Example 5

Results Concerning vatC and vgbB Genes

The *Staphylococcus cohnii* strain, BM10711, resistant to the synergistic mixtures streptogramin A and streptogramin B and related compounds (pristinamycin, virginiamycin, synergistin, milkamycin, Quinupristin-Dalfopristin) was analyzed. This strain was isolated at Douera hospital (Algeria) where the pristinamycin was frequently used topically. The strain was isolated (Liassin et al., 1997) from a sample provided from a cupboard located in a room occupied by patients suffering from chronic osteomyelitis.

The strain BM10711 harbored several plasmids including pIP1714 (5 kb). This plasmid was isolated by electroporation in a *S. aureus* recipient strain, RN4220. The transformant, harboring pIP1714, was selected on BHIA containing 10 μg/ml pristinamycin IIA. Plasmid pIP1714 conferred resistances to streptogramin A and streptogramin B and related compounds.

Plasmid pIP1714 was linearized by cleavage with HindIII and cloned in the HindIII site of the vector pOX7 also named pOX300 (Dyke et al., 1989, FEMS Microbiol. Lett. 58:209–216). pOX7 results from the cointegration of the *E. coli* vector, pUC18, and *S. aureus* plasmid, pE194. The recombinant plasmid pIP1715 consisting of pOX7 and pIP1714 was used to sequence pIP1714 in its entirety. The gene vatC (636 nucleotides) encoding an acetyltransferase inactiving streptogramin A and related compounds and the gene vgbB (885 nucleotides) encoding a lactonase inactiving streptogramin B and related compounds were found to be carried by this plasmid. The gene vatC had 71.7, 62.2 and 64.1% nucleotides identity with vat-related gene, vatB and satA respectively and the gene vgbB presents 69.5% nucleotides identity with the gene vgb.

VatC acetyltransferase exhibits significant similarity with acetyltransferases having the same enzymatic activity and encoded by the genes vatC, vatB, and sat (respectively 69.8, 58 2 and 66.0% amino acids identity). These proteins belong to a family of xenobiotic acetyltransferases modifying various substrates including streptogramin A and related antibiotics. VgbB lactonase exhibits as well significant similarity with Vgb inactivating streptogramin B and related (67.0% amino acids identity).

The two other genes carried by pIP1714 are pre and repB, encoding proteins involved in mobilization and replication, respectively. These two genes are homologous to those carried by the staphylococcal plasmid, pUB110 (McKenzie et al., 1986, Plasmid 15:93–103) Moreover, as reported in FIG. 5, the intergenic sequences of pIP1714 delimited by vatC and repB also exhibited significant similarities with pUB110.

Example 6

Plasmid DNA Isolation from PIIA$^R$ Staphylococci

The staphylococci were grown after overnight incubation at 37° C. in 200 ml BHI containing 10 μg/ml of PIIA. After 15 min centrifugation at 8000 rpm, the pellet was resuspended in 25 ml TES (Tris 50 mM, EDTA 1 mM, saccharose 7%). After adding 150 μg of lysostaphin, the mixture was incubated 30 min at 37° C. Then, 2 ml of SDS 20% and 6 ml of EDTA 0.25 M were added and the suspension was incubated 15 min at 37° C. 8 ml of NaCl 5M were added and the mixture was kept 90 min at +4° C. After 30 min centrifigation at 8000 rpm, the supernatent was incubated 15 min at 37° C. with 5 μg of Rnase (Boehringer). 10 μg of Proteinase K were added and the suspension was incubated 15 min at 65° C. DNA was precipitated using isopropanol (0.6 V for 1 V of DNA solution). After 30 min centrifugation at 8000 g, the pellet was washed with 10 ml ethanol 70%. The washed DNA was dried at 56° C., dissolved in 10 ml water and purified by dye-buoyant density centrifugation (ethidium bromide-cesium chloride). The extrachromosomal band was collected. After removing ethidium bromide, the solution of plasmid DNA was dialysed using TE buffer (Tris, 10 mM, EDTA 1 mM, pH 7).

Example 7

Plasmid DNA Isolation from E. coli

Cf. QIAfilter plasmid maxi protocol for large-scale preparations and QIAprep Spin plasmid kit protocol for mini-preparations.
Quiagen GmbH and Quiagen Inc. (Hilden, Germany).

| Plasmid maxi kit | Ref | 12262 |
| Miniprep kit | Ref | 27104 |

Example 8

Transformation by Electroporation of the S. aureus Recipient Strain, RN4220

1–Preparation of cells
200 ml of BHI was inoculated with 20 ml of an overnight culture of RN4220 (Kreiswirth et al., Nature 1983, 306: 709–712) and incubated at 37° C. with shaking. When the OD reached 0.4 at 600 nm, the suspension was kept in ice. The pellet was washed three times with 20 ml of cold Hepes buffer (saccharose 9.31%-Hepes 0.19%-pH. 7.4). The pellet was resuspended in 2.5 ml of Hepes buffer containing 10% glycerol. Aliquots of 100 μl cell suspension ($3.10^{10}$/ml) were stored at −80° C.

2—Electroporation
After thawing at room temperature, the 100 μl aliquot of cells was kept in ice. After adding 10 μl of a solution containing 1 μg of plasmid DNA, the mixture was transferred to a cold 0.2 cm electroporation cuvette. The Gene Pulser (BioRad) was set at 25 uF and 2.5 KV and the Pulse Controller to 100Ω. This produced a pulse with a constant time of 2.3 to 2.5 m sec. The cuvette was removed from the chamber and 1 ml of SOC (2% bactotryptone, 0.5% bacto-yeast extract, 10 mM NaCl, 2.5 mM KCl, 10 mM $MgCl_2$, 10 mM $MgSO_4$, 20 mM glucose) was added. The cell suspension was transferred in a propylene tube and incubated with shaking at 37° C. for 1 hr The suspension was then plated on selective medium, which consisted of BHIA containing 10 μg/ml erythromycin or 10 μg/ml of PIIA. The plates were incubated 48 h at 37° C. and the transformants isolated on selective medium. The further studies were carried out on a single isolated colony. Example 9

Polymerase Chain Reaction

DNA was amplified by PCR in a Crocodile 11 thermal cycler (Appligène) with approximately 10 ng of cellular DNA or 1 ng of plasmid DNA. The reaction mixture contained 0.6 μM of each oligonucleotide serving as primer, 200 μM of each deoxynucleotide triphosphate, 2.5 U of Taq DNA Polymerase (Amersham, Int.), and 1× buffer (Amersham, Int.) The final reaction volume was adjusted to 100 μl with $H_2O$ and the sample was then covered by 50 μl of heavy white mineral oil (Sigma Chemical Co, St. Louis, Mo.).

PCR experiments were carried out at high or low stringency, depending on the primers used. At high stringency, the PCR was performed with a precycle of 3 min at 95° C. and 2 min at 60° C., 30 cycles of 20 sec at 72° C., 20 sec at 95° C., 20 sec at 60° C. followed by a cycle of 1 min at 72° C. At low stringency, the PCR was performed with a precycle of 5 min at 95° C., 35 cycles of 2 min at 40° C., 1 min 30 sec at 72° C., 30 sec at 95° C. followed by a cycle of 4 min at 40° C. and 12 min at 72° C. The oligonucleotides used at high stringency are indicated in the Table below.

PRIMER (SEQ ID NO:17)
vgaB Oligo I   5'-AAGTCGACTGACAATATGAGTGGTGG-3'
                    SalI (SEQ ID NO:18)
Oligo II   5'-CTGCAGATGCCTCAACAGCATCGATATCC-3'
                PstI

```
                        -continued
    PRIMER (SEQ ID NO:19)
vatC Oligo III  5'-AT GAATTC GCAAATCAGCAAGG-3'
                      EcoRI (SEQ ID NO:20)
     Oligo IV   5'-TCGTCTC GAGCTC TAGGTCC-3'
                         SacI (SEQ ID NO:21)
vgbB Oligo V    5'-CAGCAG TCTAGA TCAGAGTGG-3'
                        XbaI (SEQ ID NO:22)
     Oligo VI   5'-CATAC GGATCC ACCTTTTCC-3'
                       BamHI
```

Example 10

Labelling of DNA Probes

Plasmid DNA was labelled with [α-$^{32}$P]dCTP (110 Tbq mmol$^{-1}$) by the random printing technique using the Megaprime DNA labelling system (Amersham).

Example 11

Blotting and Hybridization

Hybond-N+ membranes (Amersham) were used for blotting. DNA was transferred from agarose gels to the membranes by the capillary blotting method of Southern Blotting DNA was denatured and fixed to the membranes according to the protocol described in the handbook user of Hybond-N+ membranes.

Prehybridization and hybridization were done at 68° C. in a mixture containing 5×SSPE (1×SSPE is 0.3 M NaCl, 30 m tri-sodium citrate), 5× Denhardt's solution, 0.5% (w/v) SDS, and 100 μg ml$^{-1}$ salmon sperm DNA. The membranes containing DNA transferred from agarose gels were treated with 10 ng ml$^{-1}$ radiolabeled DNA probe. Washing was started with two successive immersions in 2×SSPE, 0.1% SDS, at room temperature for 10 min, followed by one immersion in 1×SSPE, 0.1% SDS, at 68° C. for 15 min. and finally by one immersion in 0.1×SSPE, 0.1% SDS, at 68° C. for 15 min The washed blots treated with the radiolabeled probe were exposed to Fuji RX film at −70° C.

Example 12

Nucleotides Sequence Determination

For vatC and vgbB, the sequencing reaction was performed by PCR amplification in a final volume of 20 μl using 500 ng of plasmid DNA, 5–10 pmoles of primer and 9.5 μl of DyeTerminators premix according to Applied Biosystems protocol. After heating to 94° C. for 2 min, the reaction was cycled as the following: 25 cycles of 30 s at 94° C., 30 s at 55° C., and 4 min at 60° C. (9600 thermal cycler Perkin Elmer). Removal of excess of DyeTerminators were performed using Quick Spin columns (Boehringer Mannheim). The samples were dried in a vacuum centrifuge and dissolved with 4 μl of deionized formamide EDTA pH 8.0 (5/1). The samples were loaded onto an Applied Biosystems 373A sequencer and run for 12 h on a 4.5% denaturing acrylamide gel.

—Primers used for sequencing the following genes:

• vatC

SEQ ID NO:23
5'-GAAATGGTTGGGAGAAGCATACC-3'

SEQ ID NO:24
5'-CAGCAATCGCGCCCGTTTG-3'

SEQ ID NO:25
5'-AATCGGCAGAATTACAAACG-3'

SEQ ID NO:26
5'-CGTTCCCAATTTCCGTGTTACC-3'

• vatB

SEQ ID NO:27
5'-GTTTCTATGCTGATCTGAATC-3'

SEQ ID NO:28
5'-GTCGTTTGTAATTCTGCCGATT-3'

SEQ ID NO:29
5'-GGTCTAAATGGCGATATATGG-3'

SEQ ID NO:30
5'-TTCGAATTCTTTTATCCTACC-3'

For vgaB. DNA was sequenced according to the instructions provided by the T7SequencingTm kit from Pharmacia Biotech (Uppsala, Sweden), procedures C and D.

—Primers used for sequencing the following genes:

• vgaB

| (SEQ ID NO:31) | (SEQ ID NO:32) |
|---|---|
| 5'-GCTTGGCAAAAGCAACC-3' | 5'-TGAATATAGGATAG-3' |
| (SEQ ID NO:33) | (SEQ ID NO:34) |
| 5'-TTGGATCAGGGCC-3' | 5'-CAATTAGAAGAACCAC-3' |
| (SEQ ID NO:35) | (SEQ ID NO:36) |
| 5'-CAATTGTTCAGCTAGG-3' | 5'-GAATTCATTCTATGG-3' |
| (SEQ ID NO:37) | (SEQ ID NO:38) |
| 5'-TACACCATTGTTACC-3' | 5'-CAAGGAATGATTAAGCC-3' |
| (SEQ ID NO:39) | (SEQ ID NO:40) |
| 5'-GATTCAGATGTTCCC-3' | 5'-TCATGGTCGCAATG-3' |
| (SEQ ID NO:41) | (SEQ ID NO:42) |
| 5'-GTTGCTTTCGTAGAAGC-3' | 5'-GTTATGTCATCCTC-3' |
| (SEQ ID NO:43) | (SEQ ID NO:44) |
| 5'-GGTTCATCTACGAGC-3' | 5'-GGATATCGATGCTG-3' |
| (SEQ ID NO:45) | (SEQ ID NO:46) |
| 5'-GCCAACTCCATTC-3' | 5'-CCTAGCTGAACAATTG-3' |
| (SEQ ID NO:47) | (SEQ ID NO:48) |
| 5'-GAAGGTGCCTGATCC-3' | 5'-ATACTAGAAATGC-3' |

EXAMPLE 13

DNA Cloning

Figure 4:
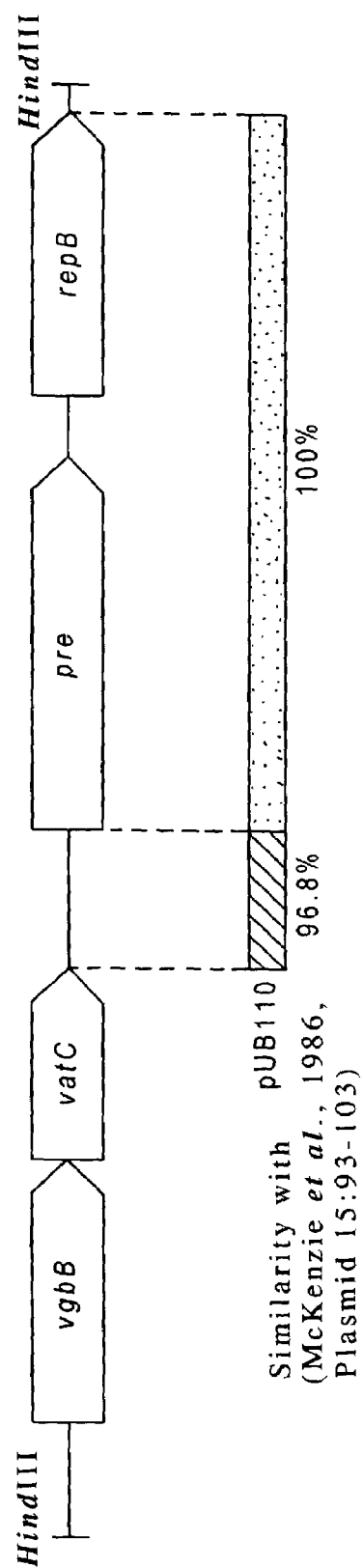
FIG. 4 is a restriction map of the plasmid pIP1714 carrying the genes vatC and vgbB as well as the genes pre and repB of *S. cohnii* strain BM10711 resistant to the synergistic mixtures of streptogramins A and B.

A standard protocol was followed for cloning into the vector pOX7, also named pOX300, the 2.4 kb HindffI-HaeIII fragment of pIP1633 carrying vgaB (FIG. 1) and the plasmid pIP1714 carrying vatC and vgbB (FIG. 4), linearized by cleavage with HindIII. The vector DNA (10–20 µg) and the plasmids used in cloning experiments were cleaved with the appropriate restriction enzymes (30 Units) and purified by GeneClean Kit (Bio 101 La Jolla, Calif.). To avoid religation, the vector cleaved with a single enzyme was dephosphorylated by 30 min incubation at 37° C. with 5 Units of alkaline phosphatase. Ligation was carried out in a total reaction volume of 10 µl containing 0.1 µl of the vector, 0.1 µg of the plasmid, 0.5 mM ATP, 1×T4 DNA ligase buffer and 0.1 Weiss Unit of T4 DNA ligase. After overnight incubation at 16° C., 1 to 2 µl of the ligation mixture are used for transforming competent E. coil and the transformants were selected on solid media containing 100 µg/ml of ampicillin.

Example 14

Susceptibility to Antimicrobial Agents

Susceptibility to antimicrobial agents was determined with a disk diffusion assay and commercially available disks (Diagnostic Pasteur) Additional disks prepared in our laboratory contained streptogramin A (20 µg) or streptogramin B (40 µg).

NCCLS: Performance standards for antimicrobial disk susceptibility test, 1984, Approved standard M2-A3, 4:369–402.

ECCLS: Standard for antimicrobial susceptibility testing by diffusion methods, 1985, ECCLS Document, 5:4–14.

Minimal inhibitory concentrations (MICs) of antibiotics were determined by serial twofold dilutions of antibiotics in MHA (Ericson H. M. and S. C. Sherris, ActaPathol. Microbiol. Scand., 1971, Suppl. 217:Section B).

Despite the relatively low frequency of detection of $SgA^R$ staphylococci (1–10%) (Loncle et al., 1993, Allignet et al., 1996), four genes encoding resistance to streptogramin A have been detected and other resistance gene(s) are suspected to be carried by staphylococci. Surprisingly, the present and previous studies (Allignet et al., 1996) indicate that staphylococcal plasmids carrying two genes encoding streptogramin A resistance by two distinct mechanisms (inactivation by acetyltransferases and increased efflux) are widespread among staphylococci (32 of the 48 plasmids investigated).

REFERENCES

The following publications have been cited herein. The entire disclosure of each publication is relied upon and incorporated by reference herein.

Allignet, J., Loncle, V., Mazodier, P. and El Solh, N (1988) Nucleotide sequence of a staphylococcal plasmid gene, vgb, encoding a hydrolase inactivating the B components of virginiamycin-like antibiotics Plasmid 20, 271–275.

Allignet, J., Loncle, V. and El Solh, N (1992) Sequence of a staphylococcal plasmid gene, vga, encoding a putative ATP-binding protein involved in resistance to virginiamycin A-like antibiotics. Gene 117, 45–51.

Allignet, J., Loncle, V., Simenel, C., Delepierre, M. and El Solh, N. (1993) Sequence of a staphylococcal gene, vat, encoding an acetyltransferase inactivating the A-type compounds of virginiamycin-like antibiotics. Gene 130, 91–98.

Allignet, J. and El Solh, N. (1995) Diversity among the Gram-positive acetyltransferases inactivating streptogramin A and structurally related compounds, and characterization of a new staphylococcal determinant, vatB. Antimicrob. Agents Chemother. 39, 2027–2036.

Allignet, J., Aubert, S., Morvan, A. and El Solh, N. (1996) Distribution of the genes encoding resistance to streptogramin A and related compounds among the staphylococci resistant to these antibiotics Antimicrob Agents Chemother-40, 2523–2528.

Allignet, J. and El Solh, N. (1996) Sequence of a staphylococcal plasmid gene vga B, encoding a putative ATP-binding protein related to vga involved in resistance to streptogramin A, 8th International Symposium on Staphylococci and Staphylococcal Infections, 23–26 June, 1996, p. 202, 239.

Aumercier, M., Bouhallab, S., Capmau, M. L. and Le Goffic, F. (1992) RP59500: a proposed mechanism for its bactericidal activity. J. Antimicrob. Chemother. 30, 9–14.

Barrasa, M. i., Tercero, J. A., Lacalle, R. A. and Jimenez, A. (1995) The ardl gene from Streptomyces capreolus encodes a polypeptide of the ABC-transporters superfamily which confers resistance to the amino-nucleotide antibiotic A201A. Eur. J. Biochem. 228, 562–569.

Blanc, V., Salah-Bey, K., Folcher, M. and Thompson, C. J. (1995) Molecular characterization and transcriptional analysis of a multidrug resistance gene cloned from the pristinamycin-producing organism, Streptomyces pristinaespiralis. Mol. Microbiol 17, 989–999.

Cocito, C. (1979) Antibiotics of the virginiamycin family, inhibitors which contain synergistic components. Microbiol. Rev. 43, 145–198.

Di Giambattista, M., Chinali, G. and Cocito, C. (1989) The molecular basis of the inhibitory activities of type A and type B synergimycins and related antibiotics on ribosomes. J. Antimicrob. Chemother. 24, 485–507.

Dyke, K. G. H. and Curnock, S. P. (1989) The nucleotide sequence of a small crypticplasmid found in Staphylococcus aureus and its relationship to other plasmids. FEMS Microbiol. Lett. 58, 209–216.

El Solh, N., Fouace, J. M., Shalita, Z., Bouanchaud, D. H., Novick, R. P. and Chabbert, Y. A. (1980) Epidemiological and structural studies of Staphylococcus aureus R plasmids mediating resistance to tobramycin and streptogramin. Plasmid 4, 117–120.

Entenza, J. M., Drugeon, H., Glauser, M. P. and Moreillon, P. (1995) Treatment of experimental endocarditis due to erythromycin-susceptible or -resistant methicillin-resistant Staphylococcus aureus with RP59500. Antimicrob. Agents Chemother 39, 1419–1424.

Fantin, B., Leclercq, R., Merl, Y., Saint-Julien, L., Veyrat, C., Duval, J. and Carbon, C. (1995) Critical influence of resistance to streptogramin B-type antibiotics on activity of RP59500 (quinupristin-dalfopristin) in experimental endocarditis due to hylococcus aureus Antimicrob. Agents Chemother. 39, 400–405.

Fierro, J. F., Vilches, C., Hardisson, C. and Salas, J. A. (1989) Streptogramins-inactivating activity in three producer streptomycetes. FEMS Microbiol. Lett. 58, 243–246.

Geistlich, M., Losick, R., Turner, J. R. and Rao, R. N. (1992) Characterization of a novel regulatory gene governing the expression of a polyketide synthase gene in Streptomyces ambofacieus. Mol. Microbiol. 6, 2019–2029.

Griswold, M W., Lomaestro, B. M. and Briceland, L. L (1.996) Quinupristin-dalfopristin (RP59500)—an injectable streptogramin combination Amer. J. Health-Syst Pharm 53, 2045–2053.

Hyde, S. C., Emsley, P., Hartshorn, M. J., Mimmack, M. M., Gileadi, U., Pearce, S. R., Gallagher, M. P., Gill, D. R, Hubbard, R. E. and Higgins, C. F. (1990) Structural model of ATP-binding proteins associated with cystic fibrosis, multidrug resistance and bacterial transport. Nature 346, 362–365.

Kim, C. H., Otake, N. and Yonehara, H. (1974) Studies on mikamycin B lactonase. I. Degradation of mikamycin B by *Streptomyces mitakaensis*. J. Antibiot. 27, 903–908.

Kloos, W. E and Schleifer, K. H. (1986). Genus IV *Staphylococcus* Rosenbach 1884. 18AL, (Nom. Cons. Opin 17 Jud. Comm. 1958, 153). In Sneath, P. H. A., Mair, N. S., Sharpe, M. E. and Holt, J. G. (Eds.), Beroey's manual of systematic bacteriology Williams & Wilkins, Baltimore, Vol 2, pp. 1013–103.

Kreiswirth, B. N., Lofdahl, S., Bethey, M. J., O'Reilly, N. M, Shlievert, P. M., Bergdoll, M. S. and Novick, R. P. (1983) The toxic shock exotoxin structural gene is not detectably transmitted by a prophage. Nature 306, 709–712.

Kyte, J. and Doolittle, R. F. (1982) A simple method for displaying the hydropathic character of a protein. J. Mol. Biol. 157, 105–132.

Liassine, N., Allignet, J. Morvan, A., Aubert, S. and El Solh, N (1997) Multiplicity of the genes and plasmids conferring resistance to pristinamycin in Staphylococci selected in an Algerian hospital, Zbl. Bakt. 1212.

Loncle, V., Casetta, A., Buu-Ho-, A. and El Solh, N (1993) Analysis of pristinamycin-resistant *Staphylococcus epidermidis* isolates responsible for an outbreak in a parisian hospital. Antimicrob. Agents Chemother. 37, 2159–2165.

MacLaughlin, J. R., Murray, C. L. and Rabinowitz, C. (1981) Unique features in the ribosome binding site sequence of the Gram-positive *Staphylococcus aureus* §-lactamase gene. J. Biol. Chem. 256, 11283–11291.

Meyer, C., Bierbaum, G., Heidrich, C., Reis, M., SŸling, J., Iglesias-Wind, M., Kempter, C., Molitor, E. and Sahl, H-G. (1995) Nucleotide sequence of the lantibiotic Pep5 biosynthetic gene cluster and functional analysis of PepP and PepC: Evidence for a role of PepC in thioether formation. Eur. J. Biochem. 232, 478–489.

Moran, C. P., Jr., Lang, N., LeGrice, S. F. J., Lee, G., Stephens, M., Sonenshein, A. L., Pero, J. and Losick, R. (1982) Nucleotide sequences that signal the initiation of transcription and translation in *Bacillus subtilis*. Mol. Gen. Genet. 186, 339–346.

Olano, C., Rodriguez, A. M., Mndez, C. and Salas, J. A. (1995) A second ABC transporter is involved in oleandomycin resistance and its secretion by *Streptomyces antibioticus*. Mol Microbiol. 16, 333–343.

Peschke, U., Schmidt, H., Zhang, H.-Z. and Piepersbergy, W. (1995) Molecular characterization of the lincomycin-production gene cluster of *Streptomyces lincolnensis* 78–11. Mol. Microbiol. 16, 1137–1156.

Rende-Fournier, R., Leclercq, R., Galimand, M., Duval, J. and Courvalin, P. (1993) identification of the satA gene encoding a streptogramin A acetyltransferase in *Enterococcus faecium* BM4145. Antimicrob. Agents Chemother. 37, 2119–2125.

Ross, J. I., Eady, E. A., Cove, J. H., Cunliffe, W. J., Baumberg, S. and Wootton, J. C. (1990) Inducible erythromycin resistance in staphylococci is encoded by a member of the ATP-binding transport super-gene family. Mol. Microbiol. 4(7), 1207–1214.

Ross, J. I., Eady, E. A., Cove, J. H. and Baumberg, S. (1995) Identification of a chromosomally encoded ABC-transport system with which the staphylococcal erythromycin exporter MsrA may interact. Gene 153, 93–98.

Ross, J. I., Eady, E. A., Cove, H H and Baumberg, S. (1996) Minimal functional system required for expression of erythromycin resistance by MSRA in *Staphyloocccus aureus* RN4220. Gene 183, 143–148.

Rosteck, P. R. J., Reynolds, P. A and Hershberger, C. L. (1991) Homology between proteins controlling *Streptomyces fradiae* tylosin resistance and ATP-binding transport Gene 102, 27–32

Sanger, F., Nicklen, S. and Coulson, A. R. (1977) DNA sequencing with chain terminating inhibitors Proc. Natl. Acad. Sci. USA 74, 5463–5467.

Schoner, B., Geistlich, M., Rosteck, P. R., Jr., Rao, R. N., Seno, E., Reynolds, P., Cox, K., Burgett, S. and Hershberger, C. (1992) Sequence similarity between macrolide-resistance determinants and ATP-binding transport proteins. Gene 115, 93–96.

Southern, E. M. (1975) Detection of specific sequences among DNA fragments separated by gel electrophoresis. J. Mol. Biol. 98, 503–517.

Tinoco, I., Jr., Borer, P. N, Dengler, B., Levine, M. D., Uhlenbeck, O. C., Crothers, D. M. and Graila, J. (1973) Improved estimation of secondary structure in ribonucleic acids. Nature New Biol. 246, 40–41.

Torralba, M. D., Frey, S. E. and Lagging, L. M. (1995) Treatment of methicillin-resistant *Staphylococcus aureus* infection with quinupristin dalfopristin. Clin. Infect. Dis. 21, 460–461.

von Heijne, G. (1986) A new method for predicting signal sequence cleavage sites. Nucl. Acids Res. 14, 4683–4690.

Walker, J. E., Saraste, M., Runswick, M. J. and Gay, N. J. (1982) Distantly related sequences in the a- and §-subunits of ATP synthase, myosin, kinases and other ATP-requiring enzymes and a common nucleotide binding fold. EMBO J. 1, 945–951.

Watson, M. E. E. (1984) Compilation of published signal sequences. Nucl. Acids Res. 12, 5145–5148.

SEQUENCE LISTING

<160> NUMBER OF SEQ ID NOS: 51

<210> SEQ ID NO 1
<211> LENGTH: 1656
<212> TYPE: DNA
<213> ORGANISM: Staphylococcus sp.

<400> SEQUENCE: 1
atgcttaaaa tcgacatgaa gaatgtaaaa aaatattatg cagataaatt aattttaaat                60

```
ataaaagaac taaagattta tagtggggat aaaataggta ttgtaggtaa gaatggagtt      120
ggcaaaacaa cacttttaaa aataataaaa ggactaatag agattgacga aggaaatata      180
attataagtg aaaaaacaac tattaaatat atctctcaat tagaagaacc acatagtaag      240
ataattgatg gaaaatatgc ttcaatattt caagttgaaa ataagtggaa tgacaatatg      300
agtggtggtg aaaaaactag atttaaacta gcagagggat ttcaagatca atgttcttta      360
atgctcgtag atgaacctac aagtaattta gatatcgaag gaatagagtt gataacaaat      420
acttttaaag agtaccgtga tacttttttg gtagtatctc atgatagaat ttttttagat      480
caagtttgta caaaaatttt tgaaattgaa atggatata ttagagaatt catcggtaat       540
tatacaaact atatagagca aaaagaaatg cttctacgaa agcaacaaga gaatacgaa       600 aagtataatt ctaaaagaaa gcaattggag caagctataa agctaaaaga gaataaggcg      660
caaggaatga ttaagccccc ttcaaaaaca atgggaacat ctgaatctag aatatggaaa      720
atgcaacatg ctactaaaca aaaaaagatg catagaaata cgaaatcgtt ggaaacacga      780
atagataaat taaatcatgt agaaaaaata aaagagcttc cttctattaa aatggattta      840
cctaatagag agcaatttca tggtcgcaat gtaattagtt taaaaaactt atctataaaa      900
tttaataatc aatttctttg gagagatgct tcatttgtca ttaaaggtgg agaaaaggtt      960
gctataattg gtaacaatgg tgtaggaaaa acaacattgt tgaagctgat tctagaaaaa     1020
gtagaatcag taataatatc accatcagtt aaaattggat acgtcagtca aaacttagat     1080
gttctacaat ctcataaatc tatcttagaa aatgttatgt ctacctccat tcaagatgaa     1140
acaatagcaa gaattgttct agcaagatta cattttatc gcaatgatgt tcataaagaa      1200
ataaatgttt tgagtggtgg agaacaaata aaggttgctt ttgccaagct atttgttagc     1260
gattgtaata cattaattct tgatgaacca acaaactatt tggatatcga tgctgttgag     1320
gcattagaag aattgttaat tacctatgaa ggtgttgtgt tatttgcttc ccatgataaa     1380
aaatttatac aaaacctagc tgaacaattg ttaataatag aaaataataa agtgaaaaaa     1440
ttcgaaggaa catatataga atatttaaaa attaaagata aaccaaaatt aaatacaaat     1500
gaaaaagaac tcaaagaaaa aaagatgata ctagaaatgc aaatttcatc attattaagt     1560
aaaatctcaa tggaagaaaa tgaagaaaaa aacaaagaat tagatgaaaa gtacaaattg     1620
aaattaaaag aattgaaaag cctaaataaa aatatt                               1656
```

<210> SEQ ID NO 2
<211> LENGTH: 636
<212> TYPE: DNA
<213> ORGANISM: Staphylococcus sp.

<400> SEQUENCE: 2

```
atgaaatggc aaaatcagca aggccccaat ccagaagaaa tataccctat agaaggtaat       60
aaacatgttc aatttattaa accatctata acaaagccca atattttagt tggggaatat      120
tcatattacg atagtaaaga tggtgaatct tttgaaagcc aagttcttta tcactatgaa      180
ttgattgggg ataaactaat attagggaag ttttgttcta ttggacccgg aacgacattt      240
ataatgaatg gggctaatca tcgtatggat ggttcaacat ttccattcaa tcttttcgga      300
aatggttggg agaagcatac ccctacattg gaagaccttc cttataaggg taacacggaa      360
attgggaacg atgtttggat tggacgagat gtgacaatta tgcccggtgt aaaaatagga      420 aacgggcta ttattgcagc aaaatcggtt gtgacaaaga acgttgatcc ttattcagtt       480
gttggcggta atccttcacg attaattaag ataaggtttt ccaaggaaaa aatcgcagca     540
```

```
ttactaaaag taaggtggtg ggacctagag atagagacga taaatgaaaa tattgattgc    600
atcctgaatg gtgatataaa aaaggttaaa agaagt                              636
```

<210> SEQ ID NO 3
<211> LENGTH: 885
<212> TYPE: DNA
<213> ORGANISM: Staphylococcus sp.

<400> SEQUENCE: 3

```
atgaattttt atttagagga gtttaacttg tctattcccg attcaggtcc atacggtata     60
acttcatcag aagacggaaa ggtatggttc acacaacata aggcaaacaa atcagcagt    120
ctagatcaga gtggtaggat aaaagaattc gaagttccta cccctgatgc taaagtgatg   180
tgtttaattg tatcttcact tggagacata tggtttacag agaatggtgc aaataaaatc   240
ggaaagctct caaaaaaagg tggctttaca gaatatccat gccacagcc ggattctggt    300
ccttacggaa taacggaagg tctaaatggc gatatatggt ttacccaatt gaatggagat   360
cgtataggaa agttgacagc tgatgggact atttatgaat atgatttgcc aaataaggga   420
tcttatcctg cttttattac tttaggttcg gataacgcac tttggttcac ggagaaccaa   480
aataattcta ttggaaggat tacaaataca gggaaattag aagaatatcc tctaccaaca   540
aatgcagcgg ctccagtggg tatcactagt ggtaacgatg gtgcactctg gtttgtcgaa   600
attatgggca acaaaatagg tcgaatcact acaactggtg agattagcga atatgatatt   660
ccaactccaa acgcacgtcc acacgctata accgcgggga aaaatagcga aatatggttt   720
actgaatggg gggcaaatca atcggcaga attacaaacg acaaaacaat tcaagaatat   780
caacttcaaa cagaaaatgc ggaacctcat ggtattacct ttggaaaaga tggatccgta   840
tggtttgcat taaatgtaa aattgggaag ctgaatttga acgaa                    885
```

<210> SEQ ID NO 4
<211> LENGTH: 552
<212> TYPE: PRT
<213> ORGANISM: Staphylococcus sp.

<400> SEQUENCE: 4

```
Met Leu Lys Ile Asp Met Lys Asn Val Lys Lys Tyr Tyr Ala Asp Lys
  1               5                  10                  15

Leu Ile Leu Asn Ile Lys Glu Leu Lys Ile Tyr Ser Gly Asp Lys Ile
             20                  25                  30

Gly Ile Val Gly Lys Asn Gly Val Gly Lys Thr Thr Leu Leu Lys Ile
         35                  40                  45

Ile Lys Gly Leu Ile Glu Ile Asp Glu Gly Asn Ile Ile Ile Ser Glu
     50                  55                  60

Lys Thr Thr Ile Lys Tyr Ile Ser Gln Leu Glu Glu Pro His Ser Lys
 65                  70                  75                  80

Ile Ile Asp Gly Lys Tyr Ala Ser Ile Phe Gln Val Glu Asn Lys Trp
                 85                  90                  95

Asn Asp Asn Met Ser Gly Gly Glu Lys Thr Arg Phe Lys Leu Ala Glu
            100                 105                 110

Gly Phe Gln Asp Gln Cys Ser Leu Met Leu Val Asp Glu Pro Thr Ser
        115                 120                 125

Asn Leu Asp Ile Glu Gly Ile Glu Leu Ile Thr Asn Thr Phe Lys Glu
    130                 135                 140

Tyr Arg Asp Thr Phe Leu Val Val Ser His Asp Arg Ile Phe Leu Asp
```

-continued

```
            145                 150                 155                 160
      Gln Val Cys Thr Lys Ile Phe Glu Ile Glu Asn Gly Tyr Ile Arg Glu
                      165                 170                 175

Phe Ile Gly Asn Tyr Thr Asn Tyr Ile Glu Gln Lys Glu Met Leu Leu
                      180                 185                 190

Arg Lys Gln Gln Glu Glu Tyr Glu Lys Tyr Asn Ser Lys Arg Lys Gln
                      195                 200                 205

Leu Glu Gln Ala Ile Lys Leu Lys Glu Asn Lys Ala Gln Gly Met Ile
                      210                 215                 220

Lys Pro Pro Ser Lys Thr Met Gly Thr Ser Glu Ser Arg Ile Trp Lys
      225                 230                 235                 240

Met Gln His Ala Thr Lys Gln Lys Lys Met His Arg Asn Thr Lys Ser
                      245                 250                 255

Leu Glu Thr Arg Ile Asp Lys Leu Asn His Val Glu Lys Ile Lys Glu
                      260                 265                 270

Leu Pro Ser Ile Lys Met Asp Leu Pro Asn Arg Glu Gln Phe His Gly
                      275                 280                 285

Arg Asn Val Ile Ser Leu Lys Asn Leu Ser Ile Lys Phe Asn Asn Gln
                      290                 295                 300

Phe Leu Trp Arg Asp Ala Ser Phe Val Ile Lys Gly Gly Glu Lys Val
      305                 310                 315                 320

Ala Ile Ile Gly Asn Asn Gly Val Gly Lys Thr Thr Leu Leu Lys Leu
                      325                 330                 335

Ile Leu Glu Lys Val Glu Ser Val Ile Ser Pro Ser Val Lys Ile
                      340                 345                 350

Gly Tyr Val Ser Gln Asn Leu Asp Val Leu Gln Ser His Lys Ser Ile
                      355                 360                 365

Leu Glu Asn Val Met Ser Thr Ser Ile Gln Asp Glu Thr Ile Ala Arg
                      370                 375                 380

Ile Val Leu Ala Arg Leu His Phe Tyr Arg Asn Asp Val His Lys Glu
      385                 390                 395                 400

Ile Asn Val Leu Ser Gly Gly Glu Gln Ile Lys Val Ala Phe Ala Lys
                      405                 410                 415

Leu Phe Val Ser Asp Cys Asn Thr Leu Ile Leu Asp Glu Pro Thr Asn
                      420                 425                 430

Tyr Leu Asp Ile Asp Ala Val Glu Ala Leu Glu Glu Leu Leu Ile Thr
                      435                 440                 445

Tyr Glu Gly Val Val Leu Phe Ala Ser His Asp Lys Lys Phe Ile Gln
                      450                 455                 460

Asn Leu Ala Glu Gln Leu Leu Ile Ile Glu Asn Asn Lys Val Lys Lys
      465                 470                 475                 480

Phe Glu Gly Thr Tyr Ile Glu Tyr Leu Lys Ile Lys Asp Lys Pro Lys
                      485                 490                 495

Leu Asn Thr Asn Glu Lys Glu Leu Lys Glu Lys Met Ile Leu Glu
                      500                 505                 510

Met Gln Ile Ser Ser Leu Leu Ser Lys Ile Ser Met Glu Glu Asn Glu
                      515                 520                 525

Glu Lys Asn Lys Glu Leu Asp Glu Lys Tyr Lys Leu Lys Leu Lys Glu
                      530                 535                 540

Leu Lys Ser Leu Asn Lys Asn Ile
      545                 550

<210> SEQ ID NO 5
```

<211> LENGTH: 212
<212> TYPE: PRT
<213> ORGANISM: Staphylococcus sp.

<400> SEQUENCE: 5

```
Met Lys Trp Gln Asn Gln Gln Gly Pro Asn Pro Glu Glu Ile Tyr Pro
 1               5                  10                  15

Ile Glu Gly Asn Lys His Val Gln Phe Ile Lys Pro Ser Ile Thr Lys
                20                  25                  30

Pro Asn Ile Leu Val Gly Glu Tyr Ser Tyr Asp Ser Lys Asp Gly
            35                  40                  45

Glu Ser Phe Glu Ser Gln Val Leu Tyr His Tyr Glu Leu Ile Gly Asp
     50                  55                  60

Lys Leu Ile Leu Gly Lys Phe Cys Ser Ile Gly Pro Gly Thr Thr Phe
 65                  70                  75                  80

Ile Met Asn Gly Ala Asn His Arg Met Asp Gly Ser Thr Phe Pro Phe
                85                  90                  95

Asn Leu Phe Gly Asn Gly Trp Glu Lys His Thr Pro Thr Leu Glu Asp
            100                 105                 110

Leu Pro Tyr Lys Gly Asn Thr Glu Ile Gly Asn Asp Val Trp Ile Gly
        115                 120                 125

Arg Asp Val Thr Ile Met Pro Gly Val Lys Ile Gly Asn Gly Ala Ile
130                 135                 140

Ile Ala Ala Lys Ser Val Val Thr Lys Asn Val Asp Pro Tyr Ser Val
145                 150                 155                 160

Val Gly Gly Asn Pro Ser Arg Leu Ile Lys Ile Arg Phe Ser Lys Glu
                165                 170                 175

Lys Ile Ala Ala Leu Leu Lys Val Arg Trp Trp Asp Leu Glu Ile Glu
            180                 185                 190

Thr Ile Asn Glu Asn Ile Asp Cys Ile Leu Asn Gly Asp Ile Lys Lys
        195                 200                 205

Val Lys Arg Ser
210
```

<210> SEQ ID NO 6
<211> LENGTH: 294
<212> TYPE: PRT
<213> ORGANISM: Staphylococcus sp.

<400> SEQUENCE: 6

```
Met Asn Phe Tyr Leu Glu Glu Phe Asn Leu Ser Ile Pro Asp Ser Gly
 1               5                  10                  15

Pro Tyr Gly Ile Thr Ser Ser Glu Asp Gly Lys Val Trp Phe Thr Gln
                20                  25                  30

His Lys Ala Asn Lys Ile Ser Ser Leu Asp Gln Ser Gly Arg Ile Lys
            35                  40                  45

Glu Phe Glu Val Pro Thr Pro Asp Ala Lys Val Met Cys Leu Ile Val
        50                  55                  60

Ser Ser Leu Gly Asp Ile Trp Phe Thr Glu Asn Gly Ala Asn Lys Ile
 65                  70                  75                  80

Gly Lys Leu Ser Lys Lys Gly Phe Thr Glu Tyr Pro Leu Pro Gln
                85                  90                  95

Pro Asp Ser Gly Pro Gly Ile Thr Glu Gly Leu Asn Gly Asp Ile Trp
            100                 105                 110

Phe Thr Gln Leu Asn Gly Asp Arg Ile Gly Lys Leu Thr Ala Asp Gly
        115                 120                 125
```

```
Thr Ile Tyr Glu Tyr Asp Leu Pro Asn Lys Gly Ser Tyr Pro Ala Phe
    130                 135                 140

Ile Thr Leu Gly Ser Asp Asn Ala Leu Trp Phe Thr Glu Asn Gln Asn
145                 150                 155                 160

Asn Ser Ile Gly Arg Ile Thr Asn Thr Gly Lys Leu Glu Glu Tyr Pro
                165                 170                 175

Leu Pro Thr Asn Ala Ala Ala Pro Val Gly Ile Thr Ser Gly Asn Asp
            180                 185                 190

Gly Ala Leu Trp Phe Val Glu Ile Met Gly Asn Lys Ile Gly Arg Ile
        195                 200                 205

Thr Thr Thr Gly Glu Ile Ser Glu Tyr Asp Ile Pro Thr Pro Asn Ala
    210                 215                 220

Arg Pro His Ala Ile Thr Ala Gly Lys Asn Ser Glu Ile Trp Phe Thr
225                 230                 235                 240

Glu Trp Gly Ala Asn Gln Ile Gly Arg Ile Thr Asn Asp Lys Thr Ile
                245                 250                 255

Gln Glu Tyr Gln Leu Gln Thr Glu Asn Ala Glu Pro His Gly Ile Thr
            260                 265                 270

Phe Gly Lys Asp Gly Ser Val Trp Phe Ala Leu Lys Cys Lys Ile Gly
        275                 280                 285

Lys Leu Asn Leu Asn Glu
    290

<210> SEQ ID NO 7
<211> LENGTH: 7
<212> TYPE: PRT
<213> ORGANISM: Staphylococcus sp.

<400> SEQUENCE: 7

Lys Ser Ile Leu Glu Asn Val
 1               5

<210> SEQ ID NO 8
<211> LENGTH: 10
<212> TYPE: PRT
<213> ORGANISM: Staphylococcus sp.
<220> FEATURE:
<221> NAME/KEY: MOD_RES
<222> LOCATION: (3)
<223> OTHER INFORMATION: Thr or Ser
<220> FEATURE:
<221> NAME/KEY: MOD_RES
<222> LOCATION: (6)
<223> OTHER INFORMATION: Ile or Val

<400> SEQUENCE: 8

Asn Tyr Xaa Asn Tyr Xaa Glu Gln Lys Glu
 1               5                  10

<210> SEQ ID NO 9
<211> LENGTH: 9
<212> TYPE: PRT
<213> ORGANISM: Staphylococcus sp.

<400> SEQUENCE: 9

Ile Met Asn Gly Ala Asn His Arg Met
 1               5

<210> SEQ ID NO 10
<211> LENGTH: 7
<212> TYPE: PRT
```

<213> ORGANISM: Staphylococcus sp.

<400> SEQUENCE: 10

Gly Asn Asp Val Trp Ile Gly
 1               5

<210> SEQ ID NO 11
<211> LENGTH: 21
<212> TYPE: DNA
<213> ORGANISM: Staphylococcus sp.

<400> SEQUENCE: 11
aarwsyatyt tagaaaatgt t                                           21

<210> SEQ ID NO 12
<211> LENGTH: 30
<212> TYPE: DNA
<213> ORGANISM: Staphylococcus sp.

<400> SEQUENCE: 12
aattataswa actatrtwga gcaaaaagaa                                  30

<210> SEQ ID NO 13
<211> LENGTH: 27
<212> TYPE: DNA
<213> ORGANISM: Staphylococcus sp.

<400> SEQUENCE: 13
atwatgaatg gkgcwaayca tmgdatg                                     27

<210> SEQ ID NO 14
<211> LENGTH: 21
<212> TYPE: DNA
<213> ORGANISM: Staphylococcus sp.

<400> SEQUENCE: 14
ggraaygatg tdtggatwgg w                                           21

<210> SEQ ID NO 15
<211> LENGTH: 2411
<212> TYPE: DNA
<213> ORGANISM: Staphylococcus sp.
<220> FEATURE:
<221> NAME/KEY: CDS
<222> LOCATION: (700..2355, 2388..2411)

<400> SEQUENCE: 15
aagctttaat taagttagca gaagattatg gagtaatact aagaacaagt gatagtagta    60
ctaaagaaca agcaaaagaa caagctaaag atgatataat tgacttatta aaagagcaat   120
tagaatatga aaaagatcga aatgaaaaac tatcaaaact taacgataat ttattggaac   180
agttagataa aaatcaaaca ttattagatc agcaacaaag attaagtctt aatgatcaaa   240
atagtatcaa aatgttagaa tcagaattag aagaaaaaaa gaagaaaaag aagaaaaaga   300
aactaagtgg tatcatgtat tccagagaaa aaataatta tatattaaaa tgagatacaa   360
caaatgaatt agtttgtttc aataggaatt tggtaaaacc catgtacata aactttttaa   420
tttagtataa ttaaataaac aaagaaatcg aaagggtgaa atattaataa aatgatcaaa   480
taatccgtca ctaaaaagaa aattaaatat attggaaaga ttttacctaa tatatttatg   540
tctatttatt atgattggat agtttgttta tttgttatat ttcacttata taaactatcc   600
tctatttaa aaaaaggagg attttttttat gcttttgttt atttgttata tttcacttat   660

```
                                                            -continued ataaactatc ctctatttta aaaaaggag gatttttttt atg ctt aaa atc gac          714
                                           Met Leu Lys Ile Asp
                                             1               5 atg aag aat gta aaa aaa tat tat gca gat aaa tta att tta aat ata        762
Met Lys Asn Val Lys Lys Tyr Tyr Ala Asp Lys Leu Ile Leu Asn Ile
             10                  15                  20 aaa gaa cta aag att tat agt ggg gat aaa ata ggt att gta ggt aag        810
Lys Glu Leu Lys Ile Tyr Ser Gly Asp Lys Ile Gly Ile Val Gly Lys
         25                  30                  35 aat gga gtt ggc aaa aca aca ctt tta aaa ata ata aaa gga cta ata        858
Asn Gly Val Gly Lys Thr Thr Leu Leu Lys Ile Ile Lys Gly Leu Ile
     40                  45                  50 gag att gac gaa gga aat ata att ata agt gaa aaa aca act att aaa        906
Glu Ile Asp Glu Gly Asn Ile Ile Ile Ser Glu Lys Thr Thr Ile Lys
 55                  60                  65 tat atc tct caa tta gaa gaa cca cat agt aag ata att gat gga aaa        954
Tyr Ile Ser Gln Leu Glu Glu Pro His Ser Lys Ile Ile Asp Gly Lys
 70                  75                  80                  85 tat gct tca ata ttt caa gtt gaa aat aag tgg aat gac aat atg agt       1002
Tyr Ala Ser Ile Phe Gln Val Glu Asn Lys Trp Asn Asp Asn Met Ser
                 90                  95                 100 ggt ggt gaa aaa act aga ttt aaa cta gca gag gga ttt caa gat caa       1050
Gly Gly Glu Lys Thr Arg Phe Lys Leu Ala Glu Gly Phe Gln Asp Gln
             105                 110                 115 tgt tct tta atg ctc gta gat gaa cct aca agt aat tta gat atc gaa       1098
Cys Ser Leu Met Leu Val Asp Glu Pro Thr Ser Asn Leu Asp Ile Glu
         120                 125                 130 gga ata gag ttg ata aca aat act ttt aaa gag tac cgt gat act ttt       1146
Gly Ile Glu Leu Ile Thr Asn Thr Phe Lys Glu Tyr Arg Asp Thr Phe
     135                 140                 145 ttg gta gta tct cat gat aga att ttt tta gat caa gtt tgt aca aaa       1194
Leu Val Val Ser His Asp Arg Ile Phe Leu Asp Gln Val Cys Thr Lys
150                 155                 160                 165 att ttt gaa att gaa aat gga tat att aga gaa ttc atc ggt aat tat       1242
Ile Phe Glu Ile Glu Asn Gly Tyr Ile Arg Glu Phe Ile Gly Asn Tyr
                 170                 175                 180 aca aac tat ata gag caa aaa gaa atg ctt cta cga aag caa caa gaa       1290
Thr Asn Tyr Ile Glu Gln Lys Glu Met Leu Leu Arg Lys Gln Gln Glu
             185                 190                 195 gaa tac gaa aag tat aat tct aaa aga aag caa ttg gag caa gct ata       1338
Glu Tyr Glu Lys Tyr Asn Ser Lys Arg Lys Gln Leu Glu Gln Ala Ile
         200                 205                 210 aag cta aaa gag aat aag gcg caa gga atg att aag ccc cct tca aaa       1386
Lys Leu Lys Glu Asn Lys Ala Gln Gly Met Ile Lys Pro Pro Ser Lys
     215                 220                 225 aca atg gga aca tct gaa tct aga ata tgg aaa atg caa cat gct act       1434
Thr Met Gly Thr Ser Glu Ser Arg Ile Trp Lys Met Gln His Ala Thr
230                 235                 240                 245 aaa caa aaa aag atg cat aga aat acg aaa tcg ttg gaa aca cga ata       1482
Lys Gln Lys Lys Met His Arg Asn Thr Lys Ser Leu Glu Thr Arg Ile
                 250                 255                 260 gat aaa tta aat cat gta gaa aaa ata aaa gag ctt cct tct att aaa       1530
Asp Lys Leu Asn His Val Glu Lys Ile Lys Glu Leu Pro Ser Ile Lys
             265                 270                 275 atg gat tta cct aat aga gag caa ttt cat ggt cgc aat gta att agt       1578
Met Asp Leu Pro Asn Arg Glu Gln Phe His Gly Arg Asn Val Ile Ser
         280                 285                 290 tta aaa aac tta tct ata aaa ttt aat aat caa ttt ctt tgg aga gat       1626
Leu Lys Asn Leu Ser Ile Lys Phe Asn Asn Gln Phe Leu Trp Arg Asp
```

-continued

```
                                    295                 300                 305
gct tca ttt gtc att aaa ggt gga gaa aag gtt gct ata att ggt aac         1674
Ala Ser Phe Val Ile Lys Gly Gly Glu Lys Val Ala Ile Ile Gly Asn
310                 315                 320                 325 aat ggt gta gga aaa aca aca ttg ttg aag ctg att cta gaa aaa gta         1722
Asn Gly Val Gly Lys Thr Thr Leu Leu Lys Leu Ile Leu Glu Lys Val
                330                 335                 340 gaa tca gta ata ata tca cca tca gtt aaa att gga tac gtc agt caa         1770
Glu Ser Val Ile Ile Ser Pro Ser Val Lys Ile Gly Tyr Val Ser Gln
            345                 350                 355 aac tta gat gtt cta caa tct cat aaa tct atc tta gaa aat gtt atg         1818
Asn Leu Asp Val Leu Gln Ser His Lys Ser Ile Leu Glu Asn Val Met
        360                 365                 370 tct acc tcc att caa gat gaa aca ata gca aga att gtt cta gca aga         1866
Ser Thr Ser Ile Gln Asp Glu Thr Ile Ala Arg Ile Val Leu Ala Arg
375                 380                 385 tta cat ttt tat cgc aat gat gtt cat aaa gaa ata aat gtt ttg agt         1914
Leu His Phe Tyr Arg Asn Asp Val His Lys Glu Ile Asn Val Leu Ser
390                 395                 400                 405 ggt gga gaa caa ata aag gtt gct ttt gcc aag cta ttt gtt agc gat         1962
Gly Gly Glu Gln Ile Lys Val Ala Phe Ala Lys Leu Phe Val Ser Asp
                410                 415                 420 tgt aat aca tta att ctt gat gaa cca aca aac tat ttg gat atc gat         2010
Cys Asn Thr Leu Ile Leu Asp Glu Pro Thr Asn Tyr Leu Asp Ile Asp
            425                 430                 435 gct gtt gag gca tta gaa gaa ttg tta att acc tat gaa ggt gtt gtg         2058
Ala Val Glu Ala Leu Glu Glu Leu Leu Ile Thr Tyr Glu Gly Val Val
        440                 445                 450 tta ttt gct tcc cat gat aaa aaa ttt ata caa aac cta gct gaa caa         2106
Leu Phe Ala Ser His Asp Lys Lys Phe Ile Gln Asn Leu Ala Glu Gln
455                 460                 465 ttg tta ata ata gaa aat aat aaa gtg aaa aaa ttc gaa gga aca tat         2154
Leu Leu Ile Ile Glu Asn Asn Lys Val Lys Lys Phe Glu Gly Thr Tyr
470                 475                 480                 485 ata gaa tat tta aaa att aaa gat aaa cca aaa tta aat aca aat gaa         2202
Ile Glu Tyr Leu Lys Ile Lys Asp Lys Pro Lys Leu Asn Thr Asn Glu
                490                 495                 500 aaa gaa ctc aaa gaa aaa aag atg ata cta gaa atg caa att tca tca         2250
Lys Glu Leu Lys Glu Lys Lys Met Ile Leu Glu Met Gln Ile Ser Ser
            505                 510                 515 tta tta agt aaa atc tca atg gaa gaa aat gaa gaa aaa aac aaa gaa         2298
Leu Leu Ser Lys Ile Ser Met Glu Glu Asn Glu Glu Lys Asn Lys Glu
        520                 525                 530 tta gat gaa aag tac aaa ttg aaa tta aaa gaa ttg aaa agc cta aat         2346
Leu Asp Glu Lys Tyr Lys Leu Lys Leu Lys Glu Leu Lys Ser Leu Asn
535                 540                 545 aaa aat att taaaataaat tatattaata ggaggtttaa aa atg aaa tat ggc         2399
Lys Asn Ile                                        Met Lys Tyr Gly
550                                                        555 cct gat cca aat                                                         2411
Pro Asp Pro Asn
        560

<210> SEQ ID NO 16
<211> LENGTH: 1607
<212> TYPE: DNA
<213> ORGANISM: Staphylococcus sp.
<220> FEATURE:
<221> NAME/KEY: CDS
<222> LOCATION: (39..923, 947..1582)
```

<400> SEQUENCE: 16

| | | |
|---|---|---|
| aggagttttt gcgttcaaaa taattgggag gaatgtaa atg aat ttt tat tta<br>                                                                                                             Met Asn Phe Tyr Leu<br>                                                                                                              1                  5 | | 53 |
| gag gag ttt aac ttg tct att ccc gat tca ggt cca tac ggt ata act<br>Glu Glu Phe Asn Leu Ser Ile Pro Asp Ser Gly Pro Tyr Gly Ile Thr<br>                   10                   15                   20 | | 101 |
| tca tca gaa gac gga aag gta tgg ttc aca caa cat aag gca aac aaa<br>Ser Ser Glu Asp Gly Lys Val Trp Phe Thr Gln His Lys Ala Asn Lys<br>             25                   30                   35 | | 149 |
| atc agc agt cta gat cag agt ggt agg ata aaa gaa ttc gaa gtt cct<br>Ile Ser Ser Leu Asp Gln Ser Gly Arg Ile Lys Glu Phe Glu Val Pro<br>        40                   45                   50 | | 197 |
| acc cct gat gct aaa gtg atg tgt tta att gta tct tca ctt gga gac<br>Thr Pro Asp Ala Lys Val Met Cys Leu Ile Val Ser Ser Leu Gly Asp<br> 55                   60                   65 | | 245 |
| ata tgg ttt aca gag aat ggt gca aat aaa atc gga aag ctc tca aaa<br>Ile Trp Phe Thr Glu Asn Gly Ala Asn Lys Ile Gly Lys Leu Ser Lys<br>70                   75                   80                   85 | | 293 |
| aaa ggt ggc ttt aca gaa tat cca ttg cca cag ccg gat tct ggt cct<br>Lys Gly Gly Phe Thr Glu Tyr Pro Leu Pro Gln Pro Asp Ser Gly Pro<br>                   90                   95                  100 | | 341 |
| tac gga ata acg gaa ggt cta aat ggc gat ata tgg ttt acc caa ttg<br>Tyr Gly Ile Thr Glu Gly Leu Asn Gly Asp Ile Trp Phe Thr Gln Leu<br>             105                  110                  115 | | 389 |
| aat gga gat cgt ata gga aag ttg aca gct gat ggg act att tat gaa<br>Asn Gly Asp Arg Ile Gly Lys Leu Thr Ala Asp Gly Thr Ile Tyr Glu<br>        120                  125                  130 | | 437 |
| tat gat ttg cca aat aag gga tct tat cct gct ttt att act tta ggt<br>Tyr Asp Leu Pro Asn Lys Gly Ser Tyr Pro Ala Phe Ile Thr Leu Gly<br>        135                  140                  145 | | 485 |
| tcg gat aac gca ctt tgg ttc acg gag aac caa aat aat tct att gga<br>Ser Asp Asn Ala Leu Trp Phe Thr Glu Asn Gln Asn Asn Ser Ile Gly<br>150                   155                   160                   165 | | 533 |
| agg att aca aat aca ggg aaa tta gaa gaa tat cct cta cca aca aat<br>Arg Ile Thr Asn Thr Gly Lys Leu Glu Glu Tyr Pro Leu Pro Thr Asn<br>             170                  175                  180 | | 581 |
| gca gcg gct cca gtg ggt atc act agt ggt aac gat ggt gca ctc tgg<br>Ala Ala Ala Pro Val Gly Ile Thr Ser Gly Asn Asp Gly Ala Leu Trp<br>        185                  190                  195 | | 629 |
| ttt gtc gaa att atg ggc aac aaa ata ggt cga atc act aca act ggt<br>Phe Val Glu Ile Met Gly Asn Lys Ile Gly Arg Ile Thr Thr Thr Gly<br>200                   205                   210 | | 677 |
| gag att agc gaa tat gat att cca act cca aac gca cgt cca cac gct<br>Glu Ile Ser Glu Tyr Asp Ile Pro Thr Pro Asn Ala Arg Pro His Ala<br>        215                  220                  225 | | 725 |
| ata acc gcg ggg aaa aat agc gaa ata tgg ttt act gaa tgg ggg gca<br>Ile Thr Ala Gly Lys Asn Ser Glu Ile Trp Phe Thr Glu Trp Gly Ala<br>230                   235                   240                   245 | | 773 |
| aat caa atc ggc aga att aca aac gac aaa aca att caa gaa tat caa<br>Asn Gln Ile Gly Arg Ile Thr Asn Asp Lys Thr Ile Gln Glu Tyr Gln<br>        250                  255                  260 | | 821 |
| ctt caa aca gaa aat gcg gaa cct cat ggt att acc ttt gga aaa gat<br>Leu Gln Thr Glu Asn Ala Glu Pro His Gly Ile Thr Phe Gly Lys Asp<br>        265                  270                  275 | | 869 |
| gga tcc gta tgg ttt gca tta aaa tgt aaa att ggg aag ctg aat ttg<br>Gly Ser Val Trp Phe Ala Leu Lys Cys Lys Ile Gly Lys Leu Asn Leu<br>        280                  285                  290 | | 917 |

-continued

```
aac gaa tgagatggga gtgagcaata ttt atg aaa tgg caa aat cag caa      967
Asn Glu                         Met Lys Trp Gln Asn Gln Gln
295                                 300 ggc ccc aat cca gaa gaa ata tac cct ata gaa ggt aat aaa cat gtt   1015
Gly Pro Asn Pro Glu Glu Ile Tyr Pro Ile Glu Gly Asn Lys His Val
        305                 310                 315 caa ttt att aaa cca tct ata aca aag ccc aat att tta gtt ggg gaa   1063
Gln Phe Ile Lys Pro Ser Ile Thr Lys Pro Asn Ile Leu Val Gly Glu
320                 325                 330 tat tca tat tac gat agt aaa gat ggt gaa tct ttt gaa agc caa gtt   1111
Tyr Ser Tyr Tyr Asp Ser Lys Asp Gly Glu Ser Phe Glu Ser Gln Val
335                 340                 345                 350 ctt tat cac tat gaa ttg att ggg gat aaa cta ata tta ggg aag ttt   1159
Leu Tyr His Tyr Glu Leu Ile Gly Asp Lys Leu Ile Leu Gly Lys Phe
                355                 360                 365 tgt tct att gga ccc gga acg aca ttt ata atg aat ggg gct aat cat   1207
Cys Ser Ile Gly Pro Gly Thr Thr Phe Ile Met Asn Gly Ala Asn His
            370                 375                 380 cgt atg gat ggt tca aca ttt cca ttc aat ctt ttc gga aat ggt tgg   1255
Arg Met Asp Gly Ser Thr Phe Pro Phe Asn Leu Phe Gly Asn Gly Trp
        385                 390                 395 gag aag cat acc cct aca ttg gaa gac ctt cct tat aag ggt aac acg   1303
Glu Lys His Thr Pro Thr Leu Glu Asp Leu Pro Tyr Lys Gly Asn Thr
400                 405                 410 gaa att ggg aac gat gtt tgg att gga cga gat gtg aca att atg ccc   1351
Glu Ile Gly Asn Asp Val Trp Ile Gly Arg Asp Val Thr Ile Met Pro
415                 420                 425                 430 ggt gta aaa ata gga aac ggg gct att att gca gca aaa tcg gtt gtg   1399
Gly Val Lys Ile Gly Asn Gly Ala Ile Ile Ala Ala Lys Ser Val Val
                435                 440                 445 aca aag aac gtt gat cct tat tca gtt gtt ggc ggt aat cct tca cga   1447
Thr Lys Asn Val Asp Pro Tyr Ser Val Val Gly Gly Asn Pro Ser Arg
            450                 455                 460 tta att aag ata agg ttt tcc aag gaa aaa atc gca gca tta cta aaa   1495
Leu Ile Lys Ile Arg Phe Ser Lys Glu Lys Ile Ala Ala Leu Leu Lys
        465                 470                 475 gta agg tgg tgg gac cta gag ata gag acg ata aat gaa aat att gat   1543
Val Arg Trp Trp Asp Leu Glu Ile Glu Thr Ile Asn Glu Asn Ile Asp
480                 485                 490 tgc atc ctg aat ggt gat ata aaa aag gtt aaa aga agt tagaaaacga    1592
Cys Ile Leu Asn Gly Asp Ile Lys Lys Val Lys Arg Ser
495                 500                 505 attttgttta ggtta                                                  1607
```

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 17
aagtcgactg acaatatgag tggtgg                                        26

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 18
ctgcagatgc ctcaacagca tcgatatcc                   29

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 19
atgaattcgc aaatcagcaa gg                          22

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 20
tcgtctcgag ctctaggtcc                             20

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 21
cagcagtcta gatcagagtg g                           21

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 22
catacggatc cacctttcc                              20

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 23
gaaatggttg ggagaagcat acc                         23

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 24
cagcaatcgc gcccgtttg                              19

<210> SEQ ID NO 25
<211> LENGTH: 20
<212> TYPE: DNA

```
<213> ORGANISM: Artificial Sequence
<220> FEATURE:
<223> OTHER INFORMATION: Description of Artificial Sequence: Primer

<400> SEQUENCE: 25
aatcggcaga attacaaacg                                                    20

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 26
cgttcccaat ttccgtgtta cc                                                 22

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 27
gtttctatgc tgatctgaat c                                                  21

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 28
gtcgtttgta attctgccga tt                                                 22

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 29
ggtctaaatg gcgatatatg g                                                  21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 30
ttcgaattct tttatcctac c                                                  21

<210> SEQ ID NO 31
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 31
gcttggcaaa agcaacc                                                       17
```

```
<210> SEQ ID NO 32
<211> LENGTH: 14
<212> TYPE: DNA
<213> ORGANISM: Artificial Sequence
<220> FEATURE:
<223> OTHER INFORMATION: Description of Artificial Sequence: Primer

<400> SEQUENCE: 32
tgaatatagg atag                                                        14

<210> SEQ ID NO 33
<211> LENGTH: 13
<212> TYPE: DNA
<213> ORGANISM: Artificial Sequence
<220> FEATURE:
<223> OTHER INFORMATION: Description of Artificial Sequence: Primer

<400> SEQUENCE: 33
ttggatcagg gcc                                                         13

<210> SEQ ID NO 34
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 34
caattagaag aaccac                                                      16

<210> SEQ ID NO 35
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 35
caattgttca gctagg                                                      16

<210> SEQ ID NO 36
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 36
gaattcattc tatgg                                                       15

<210> SEQ ID NO 37
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 37
tacaccattg ttacc                                                       15

<210> SEQ ID NO 38
<211> LENGTH: 17
<212> TYPE: DNA
<213> ORGANISM: Artificial Sequence
<220> FEATURE:
```

<223> OTHER INFORMATION: Description of Artificial Sequence: Primer

<400> SEQUENCE: 38
caaggaatga ttaagcc                                                      17

<210> SEQ ID NO 39
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 39
gattcagatg ttccc                                                        15

<210> SEQ ID NO 40
<211> LENGTH: 14
<212> TYPE: DNA
<213> ORGANISM: Artificial Sequence
<220> FEATURE:
<223> OTHER INFORMATION: Description of Artificial Sequence: Primer

<400> SEQUENCE: 40
tcatggtcgc aatg                                                         14

<210> SEQ ID NO 41
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 41
gttgctttcg tagaagc                                                      17

<210> SEQ ID NO 42
<211> LENGTH: 14
<212> TYPE: DNA
<213> ORGANISM: Artificial Sequence
<220> FEATURE:
<223> OTHER INFORMATION: Description of Artificial Sequence: Primer

<400> SEQUENCE: 42
gttatgtcat cctc                                                         14

<210> SEQ ID NO 43
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 43
ggttcatcta cgagc                                                        15

<210> SEQ ID NO 44
<211> LENGTH: 14
<212> TYPE: DNA
<213> ORGANISM: Artificial Sequence
<220> FEATURE:
<223> OTHER INFORMATION: Description of Artificial Sequence: Primer

<400> SEQUENCE: 44
ggatatcgat gctg                                                         14

```
<210> SEQ ID NO 45
<211> LENGTH: 13
<212> TYPE: DNA
<213> ORGANISM: Artificial Sequence
<220> FEATURE:
<223> OTHER INFORMATION: Description of Artificial Sequence: Primer

<400> SEQUENCE: 45
gccaactcca ttc                                                        13

<210> SEQ ID NO 46
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 46
cctagctgaa caattg                                                     16

<210> SEQ ID NO 47
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 47
gaaggtgcct gatcc                                                      15

<210> SEQ ID NO 48
<211> LENGTH: 13
<212> TYPE: DNA
<213> ORGANISM: Artificial Sequence
<220> FEATURE:
<223> OTHER INFORMATION: Description of Artificial Sequence: Primer

<400> SEQUENCE: 48
atactagaaa tgc                                                        13

<210> SEQ ID NO 49
<211> LENGTH: 522
<212> TYPE: PRT
<213> ORGANISM: Staphylococcus sp.

<400> SEQUENCE: 49
```

Met Lys Ile Met Leu Glu Gly Leu Asn Ile Lys His Tyr Val Gln Asp
  1               5                  10                  15

Arg Leu Leu Leu Asn Ile Asn Arg Leu Lys Ile Tyr Gln Asn Asp Arg
             20                  25                  30

Ile Gly Leu Ile Gly Lys Asn Gly Ser Gly Lys Thr Thr Leu Leu His
         35                  40                  45

Ile Leu Tyr Lys Lys Ile Val Pro Glu Gly Ile Val Lys Gln Phe
     50                  55                  60

Ser His Cys Glu Leu Ile Pro Gln Leu Lys Leu Ile Glu Ser Thr Lys
 65                  70                  75                  80

Ser Gly Gly Glu Val Thr Arg Asn Tyr Ile Arg Gln Ala Leu Asp Lys
                 85                  90                  95

Asn Pro Glu Leu Leu Ala Asp Glu Pro Thr Thr Asn Leu Asp Asn
            100                 105                 110

Asn Tyr Ile Glu Lys Leu Glu Gln Asp Leu Lys Asn Trp His Gly Ala
        115                 120                 125

```
Phe Ile Ile Val Ser His Asp Arg Ala Phe Leu Asp Asn Leu Cys Thr
    130                 135                 140

Thr Ile Trp Glu Ile Asp Glu Gly Arg Ile Thr Glu Tyr Lys Gly Asn
145                 150                 155                 160

Tyr Ser Asn Tyr Val Glu Gln Lys Glu Leu Glu Arg His Arg Glu Glu
                165                 170                 175

Leu Glu Tyr Glu Lys Tyr Glu Lys Glu Lys Lys Arg Leu Glu Lys Ala
            180                 185                 190

Ile Asn Ile Lys Glu Gln Lys Ala Gln Arg Ala Thr Lys Lys Pro Lys
        195                 200                 205

Asn Leu Ser Leu Ser Glu Gly Lys Ile Lys Gly Ala Lys Pro Tyr Phe
    210                 215                 220

Ala Gly Lys Gln Lys Lys Leu Arg Lys Thr Val Lys Ser Leu Glu Thr
225                 230                 235                 240

Arg Leu Glu Lys Leu Glu Ser Val Lys Arg Asn Glu Leu Pro Pro
                245                 250                 255

Leu Lys Met Asp Leu Val Asn Leu Glu Ser Val Lys Asn Arg Thr Ile
            260                 265                 270

Ile Arg Gly Glu Asp Val Ser Gly Thr Ile Glu Gly Arg Val Leu Trp
        275                 280                 285

Lys Ala Lys Ser Phe Ser Ile Arg Gly Gly Asp Lys Met Ala Ile Ile
    290                 295                 300

Gly Ser Asn Gly Thr Gly Lys Thr Thr Phe Ile Lys Lys Ile Val His
305                 310                 315                 320

Gly Asn Pro Gly Ile Ser Leu Ser Pro Ser Val Lys Ile Gly Tyr Phe
                325                 330                 335

Ser Gln Lys Ile Asp Thr Leu Glu Leu Asp Lys Ser Ile Leu Glu Asn
            340                 345                 350

Val Gln Ser Ser Gln Gln Asn Glu Thr Leu Ile Arg Thr Ile Leu
        355                 360                 365

Ala Arg Met His Phe Phe Arg Asp Asp Val Tyr Lys Pro Ile Ser Val
    370                 375                 380

Leu Ser Gly Gly Glu Arg Val Lys Val Ala Leu Thr Lys Val Phe Leu
385                 390                 395                 400

Ser Glu Val Asn Thr Leu Val Leu Asp Glu Pro Thr Asn Phe Leu Asp
                405                 410                 415

Met Glu Ala Ile Glu Ala Phe Glu Ser Leu Leu Lys Glu Tyr Asn Gly
            420                 425                 430

Ser Ile Ile Phe Val Ser His Asp Arg Lys Phe Ile Glu Lys Val Ala
        435                 440                 445

Thr Arg Ile Met Thr Ile Asp Asn Lys Glu Ile Lys Ile Phe Asp Gly
    450                 455                 460

Thr Tyr Glu Gln Phe Lys Gln Ala Glu Lys Pro Thr Arg Asn Ile Lys
465                 470                 475                 480

Glu Asp Lys Lys Leu Leu Leu Glu Thr Lys Ile Thr Glu Val Leu Ser
                485                 490                 495

Arg Leu Ser Ile Glu Pro Ser Glu Glu Leu Glu Gln Glu Phe Gln Asn
            500                 505                 510

Leu Ile Asn Glu Lys Arg Asn Leu Asp Lys
        515                 520

<210> SEQ ID NO 50
<211> LENGTH: 560
<212> TYPE: PRT
```

<213> ORGANISM: Staphylococcus sp.

<400> SEQUENCE: 50

```
Met Leu Lys Ile Asp Met Lys Asn Val Lys Tyr Tyr Ala Asp Lys
  1               5                  10                  15

Leu Ile Leu Asn Ile Lys Glu Leu Lys Ile Tyr Ser Gly Asp Lys Ile
                 20                  25                  30

Gly Ile Val Gly Lys Asn Gly Val Gly Lys Thr Thr Leu Leu Lys Ile
             35                  40                  45

Ile Lys Gly Leu Ile Glu Ile Asp Glu Gly Asn Ile Ile Ser Glu
 50                  55                  60

Lys Thr Thr Ile Lys Tyr Ile Ser Gln Leu Glu Pro His Ser Lys
 65                  70                  75                  80

Ile Ile Asp Gly Lys Tyr Ala Ser Ile Phe Gln Val Glu Asn Lys Trp
                 85                  90                  95

Asn Asp Asn Met Ser Gly Gly Glu Lys Thr Arg Phe Lys Leu Ala Glu
                100                 105                 110

Gly Phe Gln Asp Gln Cys Ser Leu Met Leu Val Asp Glu Pro Thr Ser
                115                 120                 125

Asn Leu Asp Ile Glu Gly Ile Glu Leu Ile Thr Asn Thr Phe Lys Glu
                130                 135                 140

Tyr Arg Asp Thr Phe Leu Val Val Ser His Asp Arg Ile Phe Leu Asp
145                 150                 155                 160

Gln Val Cys Thr Lys Ile Phe Glu Ile Glu Asn Gly Tyr Ile Arg Glu
                165                 170                 175

Phe Ile Gly Asn Tyr Thr Asn Tyr Ile Glu Gln Lys Glu Met Leu Leu
                180                 185                 190

Arg Lys Gln Gln Glu Glu Tyr Glu Lys Tyr Asn Ser Lys Arg Lys Gln
                195                 200                 205

Leu Glu Gln Ala Ile Lys Leu Lys Glu Asn Lys Ala Gln Gly Met Ile
            210                 215                 220

Lys Pro Pro Ser Lys Thr Met Gly Thr Ser Glu Ser Arg Ile Trp Lys
225                 230                 235                 240

Met Gln His Ala Thr Lys Gln Lys Lys Met His Arg Asn Thr Lys Ser
                245                 250                 255

Leu Glu Thr Arg Ile Asp Lys Leu Asn His Val Glu Lys Ile Lys Glu
                260                 265                 270

Leu Pro Ser Ile Lys Met Asp Leu Pro Asn Arg Glu Gln Phe His Gly
                275                 280                 285

Arg Asn Val Ile Ser Leu Lys Asn Leu Ser Ile Lys Phe Asn Asn Gln
            290                 295                 300

Phe Leu Trp Arg Asp Ala Ser Phe Val Ile Lys Gly Gly Glu Lys Val
305                 310                 315                 320

Ala Ile Ile Gly Asn Asn Gly Val Gly Lys Thr Thr Leu Leu Lys Leu
                325                 330                 335

Ile Leu Glu Lys Val Glu Ser Val Ile Ile Ser Pro Ser Val Lys Ile
                340                 345                 350

Gly Tyr Val Ser Gln Asn Leu Asp Val Leu Gln Ser His Lys Ser Ile
            355                 360                 365

Leu Glu Asn Val Met Ser Thr Ser Ile Gln Asp Glu Thr Ile Ala Arg
            370                 375                 380

Ile Val Leu Ala Arg Leu His Phe Tyr Arg Asn Asp Val His Lys Glu
385                 390                 395                 400
```

```
Ile Asn Val Leu Ser Gly Gly Glu Gln Ile Lys Val Ala Phe Ala Lys
                405                 410                 415

Leu Phe Val Ser Asp Cys Asn Thr Leu Ile Leu Asp Glu Pro Thr Asn
            420                 425                 430

Tyr Leu Asp Ile Asp Ala Val Glu Ala Leu Glu Leu Leu Ile Thr
        435                 440                 445

Tyr Glu Gly Val Val Leu Phe Ala Ser His Asp Lys Lys Phe Ile Gln
    450                 455                 460

Asn Leu Ala Glu Gln Leu Leu Ile Ile Glu Asn Asn Lys Val Lys Lys
465                 470                 475                 480

Phe Glu Gly Thr Tyr Ile Glu Tyr Leu Lys Ile Lys Asp Lys Pro Lys
                485                 490                 495

Leu Asn Thr Asn Glu Lys Glu Leu Lys Glu Lys Lys Met Ile Leu Glu
                500                 505                 510

Met Gln Ile Ser Ser Leu Leu Ser Lys Ile Ser Met Glu Glu Asn Glu
            515                 520                 525

Glu Lys Asn Lys Glu Leu Asp Glu Lys Tyr Lys Leu Lys Leu Lys Glu
            530                 535                 540

Leu Lys Ser Leu Asn Lys Asn Ile Met Lys Tyr Gly Pro Asp Pro Asn
545                 550                 555                 560

<210> SEQ ID NO 51
<211> LENGTH: 507
<212> TYPE: PRT
<213> ORGANISM: Staphylococcus sp.

<400> SEQUENCE: 51

Met Asn Phe Tyr Leu Glu Glu Phe Asn Leu Ser Ile Pro Asp Ser Gly
1               5                   10                  15

Pro Tyr Gly Ile Thr Ser Ser Glu Asp Gly Lys Val Trp Phe Thr Gln
            20                  25                  30

His Lys Ala Asn Lys Ile Ser Ser Leu Asp Gln Ser Gly Arg Ile Lys
        35                  40                  45

Glu Phe Glu Val Pro Thr Pro Asp Ala Lys Val Met Cys Leu Ile Val
    50                  55                  60

Ser Ser Leu Gly Asp Ile Trp Phe Thr Glu Asn Gly Ala Asn Lys Ile
65                  70                  75                  80

Gly Lys Leu Ser Lys Lys Gly Phe Thr Glu Tyr Pro Leu Pro Gln
                85                  90                  95

Pro Asp Ser Gly Pro Tyr Gly Ile Thr Glu Gly Leu Asn Gly Asp Ile
            100                 105                 110

Trp Phe Thr Gln Leu Asn Gly Asp Arg Ile Gly Lys Leu Thr Ala Asp
        115                 120                 125

Gly Thr Ile Tyr Glu Tyr Asp Leu Pro Asn Lys Gly Ser Tyr Pro Ala
    130                 135                 140

Phe Ile Thr Leu Gly Ser Asp Asn Ala Leu Trp Phe Thr Glu Asn Gln
145                 150                 155                 160

Asn Asn Ser Ile Gly Arg Ile Thr Asn Thr Gly Lys Leu Glu Glu Tyr
                165                 170                 175

Pro Leu Pro Thr Asn Ala Ala Pro Val Gly Ile Thr Ser Gly Asn
            180                 185                 190

Asp Gly Ala Leu Trp Phe Val Glu Ile Met Gly Asn Lys Ile Gly Arg
        195                 200                 205

Ile Thr Thr Thr Gly Glu Ile Ser Glu Tyr Asp Ile Pro Thr Pro Asn
    210                 215                 220
```

```
Ala Arg Pro His Ala Ile Thr Ala Gly Lys Asn Ser Glu Ile Trp Phe
225                 230                 235                 240

Thr Glu Trp Gly Ala Asn Gln Ile Gly Arg Ile Thr Asn Asp Lys Thr
            245                 250                 255

Ile Gln Glu Tyr Gln Leu Gln Thr Glu Asn Ala Glu Pro His Gly Ile
            260                 265                 270

Thr Phe Gly Lys Asp Gly Ser Val Trp Phe Ala Leu Lys Cys Lys Ile
        275                 280                 285

Gly Lys Leu Asn Leu Asn Glu Met Lys Trp Gln Asn Gln Gln Gly Pro
    290                 295                 300

Asn Pro Glu Glu Ile Tyr Pro Ile Glu Gly Asn Lys His Val Gln Phe
305                 310                 315                 320

Ile Lys Pro Ser Ile Thr Lys Pro Asn Ile Leu Val Gly Glu Tyr Ser
                325                 330                 335

Tyr Tyr Asp Ser Lys Asp Gly Glu Ser Phe Glu Ser Gln Val Leu Tyr
            340                 345                 350

His Tyr Glu Leu Ile Gly Asp Lys Leu Ile Leu Gly Lys Phe Cys Ser
        355                 360                 365

Ile Gly Pro Gly Thr Thr Phe Ile Met Asn Gly Ala Asn His Arg Met
    370                 375                 380

Asp Gly Ser Thr Phe Pro Phe Asn Leu Phe Gly Asn Gly Trp Glu Lys
385                 390                 395                 400

His Thr Pro Thr Leu Glu Asp Leu Pro Tyr Lys Gly Asn Thr Glu Ile
                405                 410                 415

Gly Asn Asp Val Trp Ile Gly Arg Asp Val Thr Ile Met Pro Gly Val
            420                 425                 430

Lys Ile Gly Asn Gly Ala Ile Ile Ala Ala Lys Ser Val Val Thr Lys
        435                 440                 445

Asn Val Asp Pro Tyr Ser Val Val Gly Gly Asn Pro Ser Arg Leu Ile
450                 455                 460

Lys Ile Arg Phe Ser Lys Glu Lys Ile Ala Ala Leu Leu Lys Val Arg
465                 470                 475                 480

Trp Trp Asp Leu Glu Ile Glu Thr Ile Asn Glu Asn Ile Asp Cys Ile
            485                 490                 495

Leu Asn Gly Asp Ile Lys Lys Val Lys Arg Ser
            500                 505
```

What is claimed is:

1. A kit for use in detecting a bacterium having resistance to streptogramin A and related compounds, said kit comprising:
    at least one oligonucleotide probe that hybridizes specifically to a bacterium-derived polynucleotide that encodes resistance to streptogramin A and related compounds, wherein the at least one oligonucleotide probe comprises SEQ ID NO:1 or the complete complement of SEQ ID NO:1; and
    at least one reagent for performing a nucleic acid hybridization reaction.

2. The kit according to claim 1, wherein the kit further comprises a label that allows for detection of a hybridized complex formed between the oligonucleotide probe and the bacterium-derived polynucleotide that encodes resistance to streptogramin A and related compounds.

3. The kit according to claim 1, wherein the oligonucleotide probe comprises a label that allows for detection of a hybridized complex formed between said oligonucleotide probe and the bacterium-derived polynucleotide that encodes resistance to streptogramin A and related compounds.

4. A kit for use in detecting a bacterium having resistance to streptogramin A and related compounds, said kit comprising:
    at least one oligonucleotide probe that hybridizes specifically to a bacterium-derived polynucleotide that encodes resistance to streptogramin A and related compounds, wherein the at least one oligonucleotide probe comprises a sequence chosen from SEQ ID NO:17 and SEQ ID NO:18, and the complete complements of these nucleotide sequences; and
    at least one reagent for performing a nucleic acid hybridization reaction.

5. The kit according to claim 4, wherein the kit further comprises a label that allows for detection of a hybridized complex formed between the oligonucleotide probe and the bacterium-derived polynucleotide that encodes resistance to streptogramin A and related compounds.

6. The kit according to claim 4, wherein the oligonucleotide probe comprises a label that allows for detection of a hybridized complex formed between said oligonucleotide probe and the bacterium-derived polynucleotide that encodes resistance to streptogramin A and related compounds.

7. A kit for use in detecting a bacterium harboring at least one polynucleotide encoding VgaB in a biological sample, said kit comprising:

at least one oligonucleotide probe that hybridizes specifically to a bacterium-derived polynucleotide that encodes VgaB, wherein the at least one oligonucleotide probe comprises SEQ ID NO:1 or the complete complement of SEQ ID NO:1; and at least one reagent for performing a nucleic acid hybridization reaction.

8. The kit according to claim 7, wherein the kit further comprises a label that allows for detection of a hybridized complex formed between the oligonucleotide probe and the bacterium-derived polynucleotide that encodes resistance to streptogramin A and related compounds.

9. The kit according to claim 7, wherein the oligonucleotide probe comprises a label that allows for detection of a hybridized complex formed between said oligonucleotide probe and the bacterium-derived polynucleotide that encodes resistance to streptogramin A and related compounds.

10. A kit for use in detecting a bacterium harboring at least one polynucleotide encoding VgaB in a biological sample, said kit comprising:

at least one oligonucleotide probe that hybridizes specifically to a bacterium-derived polynucleotide that encodes VgaB, wherein the at least one oligonucleotide probe comprises a sequence chosen from SEQ ID NO:17 and SEQ ID NO:18, and the complete complements of these nucleotide sequences; and at least one reagent for performing a nucleic acid hybridization reaction.

11. The kit according to claim 10, wherein the kit further comprises a label that allows for detection of a hybridized complex formed between the oligonucleotide probe and the bacterium-derived polynucleotide that encodes resistance to streptogramin A and related compounds.

12. The kit according to claim 10, wherein the oligonucleotide probe comprises a label that allows for detection of a hybridized complex formed between said oligonucleotide probe and the bacterium-derived polynucleotide that encodes resistance to streptogramin A and related compounds.

* * * * *